(12) United States Patent
Ashwell et al.

(10) Patent No.: US 6,537,994 B2
(45) Date of Patent: Mar. 25, 2003

(54) HETEROCYCLIC β₃ ADRENERGIC RECEPTOR AGONISTS

(75) Inventors: Mark Anthony Ashwell, Plainsboro, NJ (US); William Ronald Solvibile, East Windsor, NJ (US)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 09/904,115

(22) Filed: Jul. 12, 2001

(65) Prior Publication Data

US 2002/0022638 A1 Feb. 21, 2002

Related U.S. Application Data

(60) Provisional application No. 60/218,700, filed on Jul. 17, 2000.

(51) Int. Cl.⁷ .................. C07D 213/38; C07D 213/56; A61K 31/44

(52) U.S. Cl. ............... 514/249; 514/255.06; 514/303; 514/312; 514/352; 544/336; 544/350; 544/406; 546/118; 546/153; 546/304; 546/308

(58) Field of Search ................... 514/357, 249, 514/255.06, 303, 312, 352; 546/334, 118, 153, 304, 308; 544/336, 350, 406

(56) References Cited

U.S. PATENT DOCUMENTS

| | | | |
|---|---|---|---|
| 4,526,786 A | | 7/1985 | Bourgery et al. |
| 4,813,998 A | | 3/1989 | Lommen et al. |
| 5,153,210 A | | 10/1992 | Ainsworth et al. |
| 5,561,142 A | * | 10/1996 | Fisher .................. 514/312 |
| 5,578,620 A | | 11/1996 | Fujita et al. |
| 5,614,523 A | | 3/1997 | Audia et al. |
| 5,741,789 A | | 4/1998 | Hibschman |
| 5,786,356 A | | 7/1998 | Bell et al. |
| 5,789,402 A | | 8/1998 | Audia et al. |
| 5,998,452 A | | 12/1999 | Ohi et al. |
| 6,069,176 A | | 5/2000 | Tsuchiya et al. |
| 6,150,378 A | | 11/2000 | Chatterjee et al. |
| 6,214,842 B1 | | 4/2001 | Malamas et al. |
| 6,288,231 B1 | | 9/2001 | Chatterjee et al. |
| 6,346,532 B1 | | 2/2002 | Maruyama et al. |
| 6,395,762 B1 | | 5/2002 | Fobare et al. |
| 6,410,734 B1 | | 6/2002 | Hu |
| 2002/0022605 A1 | | 2/2002 | Sum et al. |
| 2002/0022641 A1 | | 2/2002 | Fobare et al. |
| 2002/0028797 A1 | | 3/2002 | Sum et al. |
| 2002/0028832 A1 | | 3/2002 | Ashwell et al. |
| 2002/0028835 A1 | | 3/2002 | Hu et al. |
| 2002/0037907 A1 | | 3/2002 | Steffan et al. |
| 2002/0040023 A1 | | 4/2002 | Quagliato et al. |
| 2002/0068751 A1 | | 6/2002 | Coghlan et al. |

FOREIGN PATENT DOCUMENTS

| | | |
|---|---|---|
| EP | 0 089 154 A2 | 9/1983 |
| EP | 0 236 624 A2 | 9/1987 |
| EP | 0 449 261 A1 | 10/1991 |
| EP | 0 590 793 A1 | 4/1994 |
| EP | 0 659 737 A2 | 6/1995 |
| EP | 0 714 883 A1 | 6/1996 |
| EP | 0 764 640 A1 | 3/1997 |
| EP | 0 801 060 A1 | 10/1997 |
| FR | 2 798 126 A1 | 3/2001 |
| GB | 2 163 150 A | 2/1986 |
| GB | 2315748 A * | 2/1998 |
| WO | WO 95/29159 A1 | 11/1995 |
| WO | WO 97/41120 A1 | 11/1997 |
| WO | WO 97/46556 A1 | 12/1997 |
| WO | WO 98/22480 A1 | 5/1998 |
| WO | WO 98/32753 A1 | 7/1998 |
| WO | WO 96/65895 | 12/1999 |
| WO | WO 01/17989 A2 | 3/2001 |
| WO | WO 01/43744 A1 | 6/2001 |
| WO | WO 01/44227 A1 | 6/2001 |

OTHER PUBLICATIONS

Marc S. Berridge et al., Nucl. Med. Biol., 1992, 563–569, 19(5).
Joan M Caroon et al., J. Pharm. Sci., Jan. 1987, 32–34, 76(1).
A. Guy et al., Synthesis, Sep. 1992, 821–22.
Manabu Hori et al., J. Org. Chem., 1998, 889–894, 63.
Yunsheng Huang et al., J. Med. Chem., 1998, 2361–2370, 41.
Bernard Hulin et al., J. Med. Chem., 1992, 1853–1864, 35.
Carl Kaiser et al., J. Med. Chem., 1977, 687–692, 20(5).
Yutaka Kawashima et al., Chem. Pharm. Bull, 1995, 1132–1136, 43(7).

(List continued on next page.)

Primary Examiner—Zinna Northington Davis
(74) Attorney, Agent, or Firm—Kimberly R. Hild

(57) ABSTRACT

This invention provides compounds of Formula I having the structure

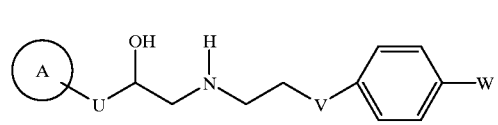

wherein,

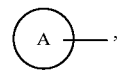

U, V, and W are as defined hereinbefore, or a pharmaceutically acceptable salt thereof, which are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension and frequent urination; and are particularly useful in the treatment or inhibition of type II diabetes.

10 Claims, No Drawings

OTHER PUBLICATIONS

Kiyoto Koguro et al., Synthesis, 1998, 910–914.
Gerard Leclerc et al., J. Med. Chem., 1980, 738–744, 23(7).
D. Mauleon et al., Il Farmaco, 1989, 1109–1117, 44(11).
Alexander McKillop et al., J. Am. Chem. Soc., Sep. 1971, 4919–4920, 93(19).
Ricardo Tapia et al., Synthetic Communications, 1986, 681–687, 16(6).
Edward C. Taylor et al., Synthesis, Aug. 1981, 606–608.
Michiaki Tominaga et al., Chem. Pharm. Bull, 1987, 3699–3704, 35(9).
R.H. Uloth et al., J. Med. Chem., 1966, 88–97, 9.
Paul C. Unangst et al., J. Med Chem., 1994, 322–328, 37.
Sophie Vanwetswinkel et al., J. Anitbiotics, Sep. 1994, 1041–1051, 47(9).
S. Tamada et al., JP 01061468 A2 (English abstract), 1989.
Michael S. Malamas et al., Medicinal Chemistry Research, 10(3), 164–177 (2000).

Ann E. Weber et al., Bioorganic & Medicinal Chemistry Letters, 8, 1101–1106, (1998).

Baihua Hu et al., Bioorganic & Medicinal Chemistry Letters, 11, 981–984 (20021).

K. Anji Reddy et al., Bioorganic & Medicinal Chemistry Letters, 8, 999–1002 (1998).

Barrie Cantello et al., J. Med. Chem., 37, 3977–3985 (1994).

Abstract of WO 99/25687A1, Accession No. 1999:350651 Caplus (1999).

Baihua Hu et al., J. Med. Chem., 44, 1456–1466 (2001).

Abstract of Papers American Chemical Society, 221, 1–2, (2001).

* cited by examiner

HETEROCYCLIC β₃ ADRENERGIC RECEPTOR AGONISTS

This application claims the benefit of U.S. Provisional Application No. 60/218,700, filed Jul. 17, 2000.

BACKGROUND OF THE INVENTION

This invention relates to heterocyclic $\beta_3$ adrenergic receptor agonists useful for the treatment of metabolic disorders related to insulin resistance or hyperglycemia (typically associated with obesity or glucose intolerance), atherosclerosis, gastrointestinal disorders, neurogenetic inflammation, glaucoma, ocular hypertension, and and frequent urination, and are particularly useful in the treatment or inhibition of type II diabetes.

The subdivision of β adrenergic receptors (β-AR) into $\beta_1$- and $\beta_2$-AR has led to the development of $\beta_1$- and $\beta_2$-antagonists and/or agonists which have been useful for the treatment of cardiovascular disease and asthma. The recent discovery of "atypical" receptors, later called $\beta_3$-AR, has led to the development of $\beta_3$-AR agnoists which may be potentially useful as antiobesity and antidiabetic agents. For recent reviews on $\beta_3$-AR agnoists, see: 1. A. D. Strosberg, Annu. Rev. *Pharmacol. Toxicol.* 1997, 37, 421; 2. A. E. Weber, *Ann. Rep. Med. Chem.* 1998, 33, 193; 3. C. P. Kordik and A. B. Reitz, *J. Med. Chem.* 1999, 42, 181; 4. C. Weyer, J. F. Gautier and E. Danforth, *Diabetes and Metabolism,* 1999, 25, 11.

Compounds that are potent and selective $\beta_3$ agonists, may be potentially useful antiobesity agents. Low levels or lack of $\beta_1$ and $\beta_2$-agonistic properties will minimize or eliminate the adverse side effects that are associated with $\beta_1$ and $\beta_2$ agonistic activities, i.e. increased heart rate, and muscle tremor, respectively.

Early developments in the $\beta_3$-agonist field are described in European patent 427480, U.S. Pat. Nos. 4,396,627, 4,478,849, 4,999,377, 5,153,210. Although the early developments purport to claim compounds with greater $\beta_3$-AR selectivity over the $\beta_1$- and $\beta_2$-AR. However, clinical trials in humans with those early developed $\beta_3$-agonists have, so far, not been successful.

More recently, potent and selective human $\beta_3$ agonists have been described in several patents and published applications: WO 98/32753, WO 97/46556, WO 97/37646, WO 97/15549, WO 97/25311, WO 96/16938, WO 95/29159, European Patents 659737, 801060, 714883, 764640, 827746, and U.S. Pat. Nos. 5,561,142, 5,705,515, 5,436,257, and 5,578,620. These compounds were evaluated in Chinese hamster ovary (CHO) cells test procedures, expressing cloned human β3 receptors, which predict the effects that can be expected in humans (Granneman et al., *Mol Pharmacol,* 1992, 42, 964; Emorine et al., *Science,* 1989, 245, 1118; Liggett *Mol. Pharmacol.,* 1992, 42, 634).

$\beta_3$-Adrenergic agonists also are useful in controlling the frequent urge of urination. It has been known that relaxation of the bladder detrusor is under beta adrenergic control (Li J H, Yasay G D and Kau S T *Pharmacology* 1992; 44: 13–18). Beta-adrenoceptor subtypes are in the detrusor of guinea-pig urinary bladder. Recently, a number of laboratories have provided experimental evidence of $\beta_3$ adrenergic receptors in a number of animal species including human (Yamazaki Y, Takeda H, Akahane M, Igawa Y, et al. *Br. J. Pharmacol.* 1998; 124: 593–599), and that activation of the $\beta_3$ receptor subtype by norepinephrine is responsible for relaxation of the urinary bladder.

Urge urinary incontinence is characterized by abnormal spontaneous bladder contractions that can be unrelated to bladder urine volume. Urge urinary incontinence is often referred to hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. Neurogenic bladders are associated with an uninhibited micturition reflex. An upper motor neuron disease is usually the underlying cause. In either case, the disease is characterized my abnormal spontaneous contractions that result in an abnormal sense of urinary urgency and involuntary urine loss. At present, the most common therapy for hyperactive bladder includes the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30%.

In the bladder, $\beta_3$ adrenergic receptor agonists activate adenylyl cyclase and generate cAMP through the G-protein coupled $\beta_3$ receptor. The resulting phosphorylation of phospholamban/calcium ATPase enhances uptake of calcium into the sarcoplasmic reticulum. The decrease in intracellular calcium inhibits bladder smooth muscle contractility.

It is suggested therefore, that activation of the $\beta_3$ adrenergic receptor in the urinary bladder will inhibit abnormal spontaneous bladder contractions and be useful for the treatment of bladder hyperactivity. Note, that unlike the antimuscarinics, $\beta_3$ adrenergic receptor agonists would be expected to be active against both neurogenic and myogenic etiologies.

Despite all these recent developments there is still no single therapy available for the treatment of type II diabetes (NIDDM), obesity, atherosclerosis, gastrointestinal disorders, neurogenetic inflammation, frequent urination and related diseases. A potent and selective $\beta_3$ adrenergic receptor agonist is therefore highly desirable for the potential treatment of such disease states.

DESCRIPTION OF THE INVENTION

This invention provides compounds of Formula I having the structure

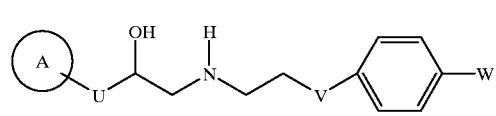

wherein,

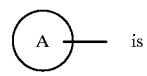 is (a) a 5–6 membered heterocyclic ring having 1–4 heteroatoms selected from O, N, and S, substituted with $(R^1)_m$;

(b) a phenyl ring substituted with $(R^1)_m$;

(c) a naphthyl ring substituted with $(R^1)_m$; or (d) a phenyl fused heterocycle selected from the group consisting of

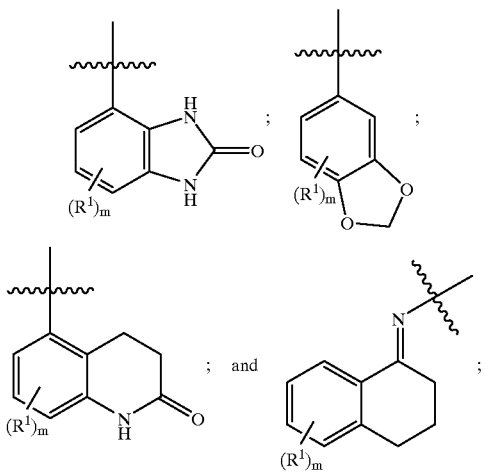

U is —OCH$_2$— or a bond;
V is O or a bond;
W is

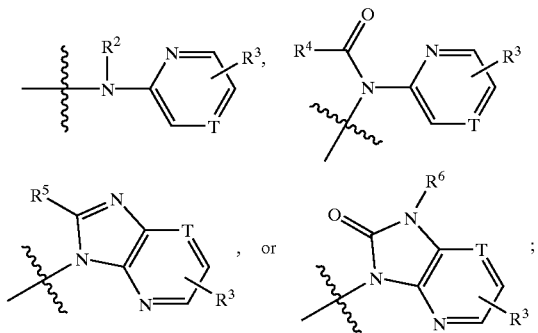

T is CH or N;
R$^1$ is alkyl of 1–8 carbon atoms, aryl of 6–10 carbon atoms, —OR$^7$, cycloalkyl of 3–8 carbon atoms, halogen, cyano, trifluoromethyl, CO$_2$R$^7$, NHCOR$^7$, NHSO$_2$R$^7$, —NR$^7$CONR$^8$R$^9$, —NR$^7$R$^8$, alkenyl of 2–7 carbon atoms, S(O)$_v$R$^7$, NO$_2$, —O(CH$_2$)$_u$CO$_2$R$^7$, —OCONR$^7$R$^8$, —O(CH$_2$)$_s$OR$^7$, or a 5–6 membered heterocyclic ring containing 1 to 4 heteroatoms selected from O, S, and N;
R$^2$, R$^4$, R$^7$, R$^8$, and R$^9$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;
R$^3$ is hydrogen, nitro, halogen, or —NR$^{10}$R$^{11}$;
R$^5$ is hydrogen; alkyl of 1–8 carbon atoms; alkenyl of 2–7 carbon atoms; arylalkyl having 1–8 carbon atoms in the alkyl moiety; alkyl of 1–8 carbon atoms, substituted with 1–4 substituents selected from —OR$^7$ and halogen; —(CH$_2$)$_q$CR$^{12}$R$^{13}$(CH$_2$)$_r$R$^7$; aryl of 6–10 carbon atoms, optionally mono-, di-, or tri-substituted with a substituent selected from the group consisting of halogen, cyano, nitro, trifluoromethyl, alkyl of 1–8 carbons optionally substituted with 1–4 substituents selected from OR$^7$ or halogen, cycloalkyl of 3–8 carbon atoms, aryl of 6–10 carbon atoms, —NHCONR$^7$R$^8$, and —CO$_2$R$^7$; or a 5–6 membered heterocyclic ring containing 1 to 4 heteroatoms selected from O, S, and N, which is optionally mono- or di-substituted with halogen, alkyl of 1–8 carbon atoms, or arylalkyl having 1–8 carbon atoms in the alkyl moiety;
R$^6$ is hydrogen, alkyl of 1–8 carbon atoms, alkenyl of 2–7 carbon atoms, or arylalkyl having 1–8 carbon atoms in the alkyl moiety;
R$^{10}$ and R$^{11}$ are each, independently, hydrogen, alkyl of 1–8 carbon atoms, arylalkyl having 1–8 carbon atoms in the alkyl moiety, —COR$^7$, or —CONR$^7$R$^8$;
R$^{12}$ and R$^{13}$ are each, independently, hydrogen, alkyl of 1–8 carbon atoms, or aryl of 6–10 carbon atoms which is optionally substituted with alkyl of 1–8 carbon atoms or halogen; or R$^{12}$ and R$^{13}$ are taken together to form a spiro fused cycloalkyl ring of 3–8 carbon atoms;
m=0–2;
q=0–5;
r=0–5;
s=1–4;
u=1–4;
v=0–2;

or a pharmaceutically acceptable salt thereof, which are selective agonists at human β$_3$ adrenergic receptors and are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

The compounds of the instant invention all contain at least one asymmetric center. Additional asymmetric centers may be present on the molecule depending upon the nature of the various substituents on the molecule. Each such asymmetric center will produce two optical isomers and all such optical isomers, as separated, pure or partially purified optical isomers or racemic mixtures thereof, are included within the scope of the instant invention. Any enantiomer of a compound of the general Formula I may be obtained by stereospecific synthesis using optically pure starting materials of know configuration. In the case of the asymmetric center represented by the asterisk in formula Ia, it has been found that the compound in which the hydroxy substituent is above the plane of the structure, is preferred over the compound in which the hydroxy substituent is below the plane of the structure.

Ia

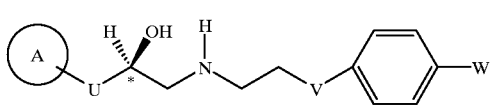

Alkyl and alkenyl include both straight chain as well as branched moieties. Halogen means bromine, chlorine, fluorine, and iodine. Aryl includes monocyclic or bicyclic aromatic carbocyclic groups such as phenyl and naphthyl. Benzyl is the preferred arylalkyl moiety.

The term heterocyclic ring may be aromatic or non-aromatic unless stated as one or the other. Further definition may be derived from the substituents of the heterocycle. The monocyclic and bicyclic heterocycles described above are unsubstituted, or mono- or di-substituted on any available carbon atoms. The heterocyclic ring may be attached within structural Formula I by any carbon atom or heteroatom.

As used herein, a heterocyclic ring is a ring confining 1–4 heteroatoms selected from N, O, and S, indicates a heterocycle which may be saturated, unsaturated, or partially unsaturated. The heterocyclic ring may be attached within structural Formula I by any carbon atom or appropriate heteroatom. It is understood that the heterocyclic ring does not contain heteroatoms in arrangements which would make them inherently unstable. For example, the term heterocyclic ring does not include ring systems containing O—O bonds in the ring backbone. Preferred 5 and 6 membered heterocycles include pyridyl, pyrimidinyl, pyrrolyl, thienyl, furyl, imidazolyl, thiazolyl, and thiadiazolyl.

Preferred compounds of Formula I are those in which

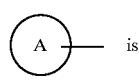 is (a) a phenyl ring substituted with $(R^1)_m$; or
(b) a phenyl fused heterocycle selected from the group consisting of

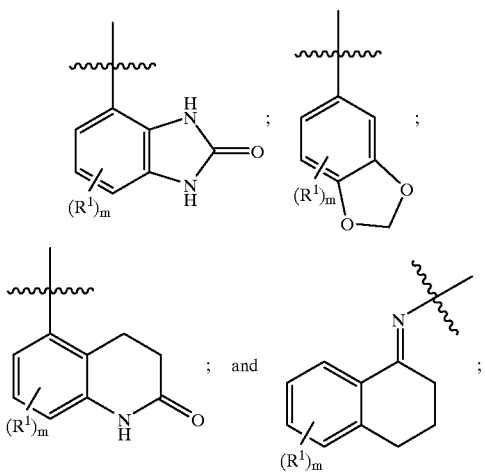

U is —OCH$_2$—;
V is O;

W is

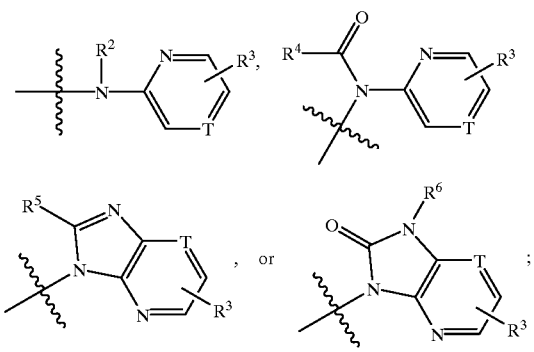

T is CH;
$R^1$ is —OR$^7$;
$R^2$, $R^4$, $R^7$, $R^8$, and $R^9$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;
$R^3$ is hydrogen, nitro, or —NR$^{10}$R$^{11}$;
$R^5$ is hydrogen; alkyl of 1–8 carbon atoms; —(CH$_2$)$_q$CR$^{12}$R$^{13}$(CH$_2$)$_r$R$^7$; aryl of 6–10 carbon atoms, optionally mono-, substituted with a substituent selected from the group consisting of halogen, alkyl of 1–8 carbons optionally substituted with 1–4 substituents selected from OR$^7$ or halogen, cycloalkyl of 3–8 carbon atoms, and —NHCONR$^7$R$^8$; or a 5–6 membered heterocyclic ring containing 1 to 4 heteroatoms selected from O, S, and N, which is optionally mono- or di-substituted with halogen, alkyl of 1–8 carbon atoms, or arylalkyl having 1–8 carbon atoms in the alkyl moiety;
$R^6$ is hydrogen, alkyl of 1–8 carbon atoms, or alkenyl of 2–7 carbon atoms;
$R^{10}$ and $R^{11}$ are each, independently, hydrogen, alkyl of 1–8 carbon atoms, —COR$^7$, or —CONR$^7$R$^8$;
$R^{12}$ and $R^{13}$ are hydrogen;
m=0–1;
q=0–5;
r=0–5;
or a pharmaceutically acceptable salt thereof.

Specifically preferred compounds of this invention are:
a) 4-((2S)-2-Hydroxy-3-{2-[4-(3-nitro-pyridin-2-ylamino)-phenyl]ethylamino}-propoxy)-phenol;
b) 4-((2R)-3-{2-[4-(3-Amino-pyridin-2-ylamino)-phenyl]-ethylamino}-2-hydroxy-propoxy)-phenol;
c) 4-{(2S)-2-Hydroxy-3-[2-(4-imidazo[4,5-b]pyridin-3-yl-phenyl)ethylamino]-propoxy}-phenol;
d) 1-Hexyl-3-[2-(4-{2-[(2S)-2-hydroxy-3-(4-hydroxy-phenoxy)-propylamino]ethyl}-phenylamino)-pyridin-3-yl]-urea;
e) 1-Hexyl-3-{4-[3-(4-{2-[(2S)-2-hydroxy-3-(4-hydroxy-phenoxy)propylamino]-ethyl}-phenyl)-3H-imidazo[4,5-b]pyridin-2-yl]-phenyl}-urea;
f) 4-[(2S)-3-(2-{4-[2-(4-Ethyl-phenyl)-imidazo[4,5-b]pyridin-3-yl]phenyl}-ethylamino)-2-hydroxy-propoxy]-phenol;
g) 4-((2S)-3-{2-[4-(3-Amino-pyridin-2-yloxy)-phenyl]-ethylamino}-2-hydroxy-propoxy)-phenol;
h) N-[2-(4-{2-[(2S)-2-Hydroxy-3-(4-hydroxy-phenoxy)-propylamino]-ethyl}phenylamino)-pyridin-3-yl]-benzamide;

i) 4-((2S)-2-Hydroxy-3-{2-[4-(2-pentyl-imidazo[4,5-b]pyridin-3-yl)phenyl]-ethylamino}-propoxy)-phenol;

j) 3-(4-{2-[(2S)-2-Hydroxy-3-(4-hydroxy-phenoxy)-propylamino]-ethyl}phenyl)-1-isopropenyl-1,3-dihydro-imidazo[4,5-b]pyridin-2-one;

k) 4-[(2S)-3-(2-{4-[2-(4-Cyclohexyl-phenyl)-imidazo[4,5-b]pyridin-3-yl]phenyl}-ethylamino)-2-hydroxy-propoxy]-phenol;

l) 4-((2S)-2-Hydroxy-3-{2-[4-(2-pentyl-imidazo[4,5-b]pyridin-3-yl)phenyl]-ethylaminol}-propoxy)-1,3-dihydro-benzoimidazol-2-one;

m) 4-[(2S)-3-(2-{4-[2-(2-Cyclopentyl-ethyl)-imidazo[4,5-b]pyridin-3-yl]phenyl}-ethylamino)-2-hydroxy-propoxy]-phenol;

n) 4-{3-[2-(4-{2-[2-Chloro-4-(3-methyl-pyrazol-1-yl)-phenyl]phenol-imidazo[4,5-b]pyridin-3-yl}-phenyl)-ethylamino]-2-hydroxy-propoxy}-;

o) 1-Hexyl-3-{3-[3-(4-{2-[2-hydroxy-3-(4-hydroxy-phenoxy)-propylamino]ethyl}-phenyl)-3H-imidazo[4,5-b]pyridin-2-yl]-phenyl urea;

p) 1-Hexyl-3-(4-{2-[3-(4-{2-[(2S)-2-hydroxy-3-(4-hydroxy-phenoxy)propylamino]-ethyl}-phenyl)-3H-imidazo[4,5-b]pyridin-2-yl]-ethyl}phenyl) urea;

q) 4-[3-(2-{4-[2-(2-Cyclopentyl-ethyl)-imidazo[4,5-b]pyridin-3-yl]phenyl}-ethylamino)-2-hydroxy-propoxy]-1,3-dihydro-benzoimidazol-2-one;

or a pharmaceutically acceptable salt thereof.

The compounds of this invention were be prepared according to the following schemes from commercially available starting materials or starting materials which can be prepared using literature procedures. These schemes show the preparation of representative compounds of this invention.

(I)

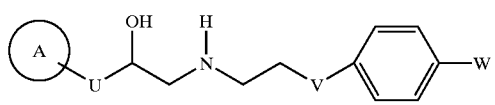

When U represents —OCH$_2$— compounds of the present invention can be prepared from epoxide intermediate such as those of Formula (II) and amine intermediates such as those of Formula (IV). The preparation of these intermediates is described in the following schemes.

(II)

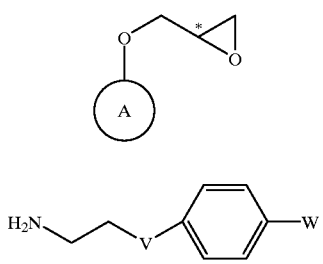

(III)

When U represents a bond compounds of the present invention can be prepared from epoxide intermediates such as those of Formula (IV) and amine intermediates of Formula (III). Alternatively, an intermediate of Formula (V) may be reacted with amine intermediates of Formula (III). The preparation of these intermediates is described in the following schemes.

(IV)

(V)

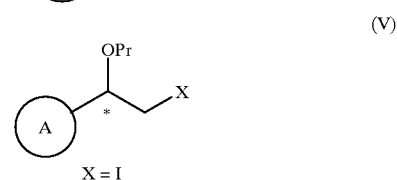

X = I

Scheme 1

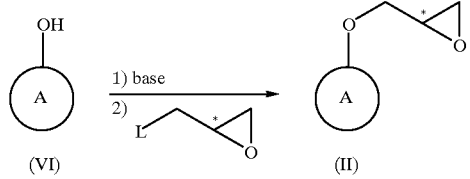

Compounds of Formula (II) can be conveniently prepared by a variety of methods familiar to those skilled in the art. One common route is illustrated in Scheme 1. Alcohol (VI) is treated with base such as sodium hydride or potassium t-butoxide in a polar solvent such as anhydrous N,N-dimethylformamide. The resulting anion is alkylated with a suitable epoxide derivative, wherein, "L" is a leaving group such as a sulfonate ester or a halide, for 0.5 to 24 hours at a temperature of 20–100° C. to provide epoxide (II). The reacting epoxide derivative is conveniently the commercially available, enantiomerically pure (2S) or (2R)-glycidyl 3-nitrobenzene sulfonate, or (2R) or (2S)-glycidyl 4-toluenesulfonate, thus both (S) and (R) enantiomers of epoxide (III) are available. J. M. Klunder et al., *J. Org. Chem.*, 1989, 54, 1295.

Scheme 2

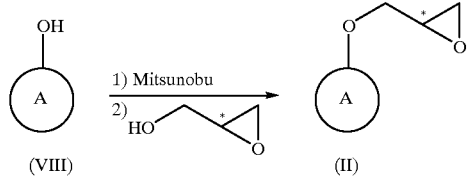

Alternatively, compounds of Formula (II) can be conveniently prepared from alcohol (VI) under Mitsunobu conditions reaction (O. Mitsunobu, *Bull. Chem. Soc. Jpn.*, 1967, 60, 2380,) reacting the commercially available, enantiomerically pure (2S) or (2R)-glycidol, with triphenyl phosphine and a dialkyl azodicarboxylate in an anhydrous solvent such as tetrahydrofuran at 20–35° C. for 12–36 hours, suitable alkyl groups are ethyl, isopropyl etc., Scheme 2.

The alcohols are commercially available or readily prepared by methods described in the literature and known to those skilled in the art. R$_1$ substitutions on the alcohol (VI) may need to be protected during the reaction with the epoxide derivatives and subsequent procedures. A description of such protecting groups may be found in: Protective Groups in Organic Synthesis, 2$^{nd}$ Ed., T. W. Greene and P. G. M. Wut, John Wiley and Sons, New York, 1991.

A useful method for protecting the preferred alcohol wherein $(R_1)_m$ is 4-hydroxyphenyl is as its tert-butyldiphenylsilyl (TBDPS) derivative shown in Scheme 3. Commercially available 4-(benzyloxy)phenol is treated with a silylating agent such as tert-butyldiphenylsilyl chloride in the presence of an organic base such as imidazole in an inert anhydrous solvent such as dichloromethane. The resulting compound (IX) is then treated under transfer hydrogenation conditions using Pd/C and cyclohexene in ethanol at reflux for 12–24 hours to prepare the alcohol (X).

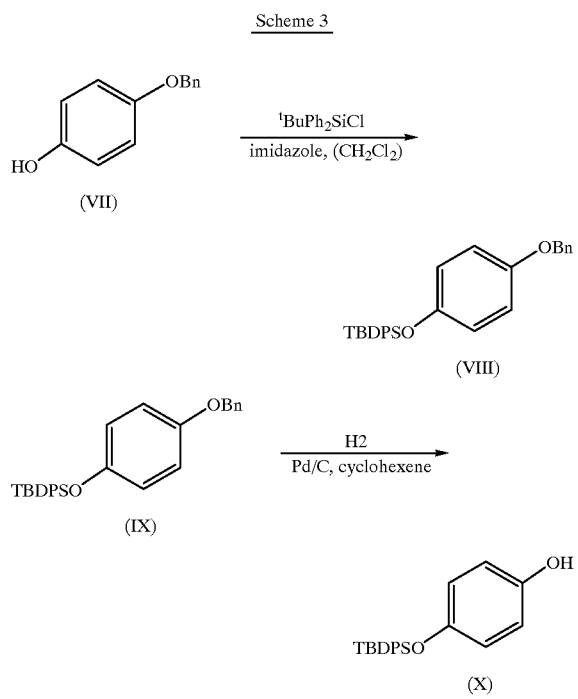

Scheme 3

Epoxides of Formula (IV) are known in the literature or may be conveniently prepared by a variety of methods familiar to those skilled in the art. One common route is shown in Scheme 4.

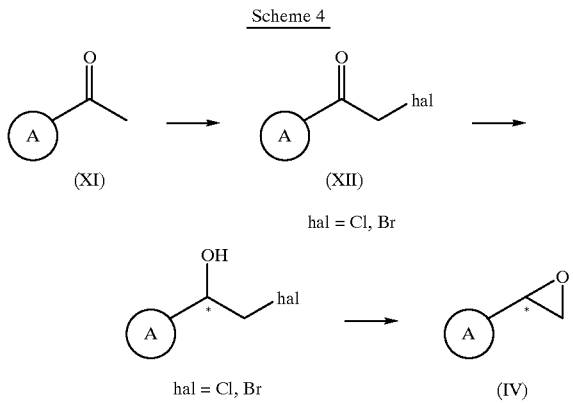

Scheme 4

Methyl ketone (XI) may be converted to the corresponding haloketone using a variety of reagents known to those skilled in the art and summarised in Larock, Comprehensive Organic Transformations, VCH, New York, 1989, 369–372. For the synthesis wherein hal=Br, bromine or dibromobarbituric acid may be used. The reduction of the haloketone is conveniently performed with a reducing agent such as sodium borohydride. The resulting alcohol when treated with a base such as sodium hydroxide or potassium carbonate in a suitable solvent such as 2-butanone or acetone yields the epoxide of Formula (IV).

The enantiomercially enriched (R) or (S)-epoxide (IV) are readily available by asymmetric reduction of haloketones (XII) using chiral reducing agents in place of sodium borohydride. Such chiral reducing agents include (−) or (+)-DIP-Cl, (R) or (S)-Alpine borane or (R) or (S)-tetrahydro-1-methyl-3,3-diphenyl-1H,3H-pyrrolo[1,2-c][1,3,21]oxazaborole-borane ((R) or (S)-OAB.BH$_3$). Alternatively the haloketones (XII) may be treated with borane in the presence of a chiral auxiliary agent such as described by E. J. Corey et al., *J. Org. Chem.*, 1991, 56, 442, Compound (V) can be conveniently prepared by substantially following the literature procedure reported by E. J. Corey and J. O. Link, *J. Org. Chem.*, 1991, 56, 422, and patent WO 9737646 wherein haloketones such as (XII) are transformed into compounds (V) by sequential halogenation, asymmetric reduction followed by transformation to the iodide and finally protection of the alcohol as a silyl ether.

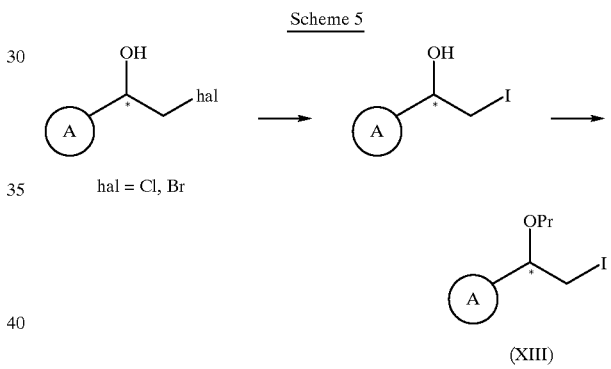

Scheme 5

The methyl ketones are commercially available or readily prepared by methods described in the literature and known to those skilled in the art. $R_1$ substitutions on the methyl ketones may need to be protected during the reaction with the epoxide derivatives and subsequent procedures. A description of such protecting groups may be found in: Protective Groups in Organic Synthesis, 2$^{nd}$ Ed., T. W. Greene and P. G. M. Wut, John Wiley and Sons, New York, 1991.

A convenient route for the preparation of amines of Formula (III) is illustrated in the following Schemes.

In order to provide intermediates which can be further transformed into amines of Formula (III) the amine group is preferentially protected. One most convenient procedure is shown in Scheme 6. Compound (XVI) is selectively protected as a carbamate derivative. Di-tert-butyl dicarbonate reacts preferentially in an inert solvent such dichloromethane at ambient temperature to provide the tert-butyl carbamate protected primary amine (XVII).

Scheme 6

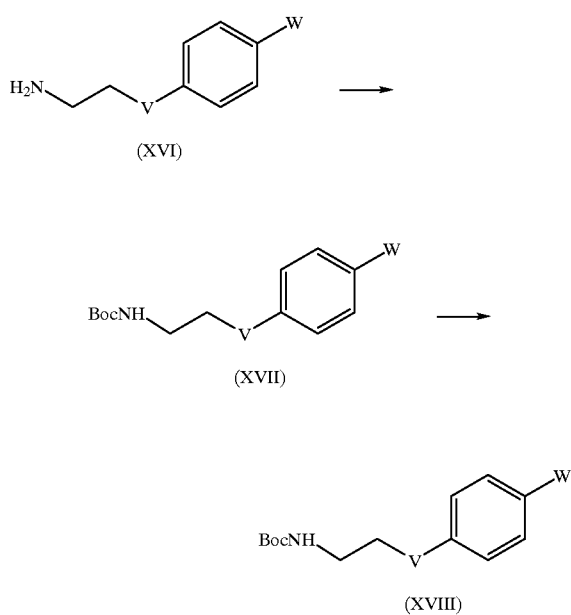

Protected amine (XVII) is able to be further transformed into compounds of Formula (XVII). The following examples serve to provide examples which illustrate but not limit the invention. Where W is pyridine then a suitable commercially available reagent is 2-chloro-3-nitropyridine. Thus heating a mixture of (XVII) and 2-chloro-3-nitropyridine either neat or in a suitable inert solvent such as N,N-diisopropylethylamine (see R. L. Clark *J. Med. Chem.,* 1978, 21, 965) provides (XIX) as shown in Scheme 7.

Scheme 7

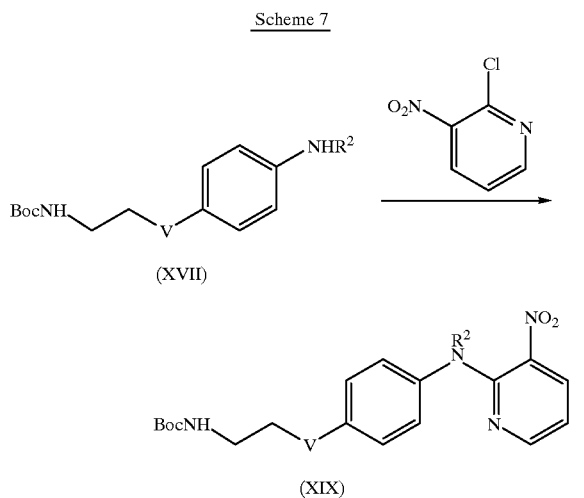

When W is pyrmidine then the commercially available 2,6-dichloropyrazine serves to establish the new W-heterocycle bond in an analogous fashion, Scheme 8.

Scheme 8

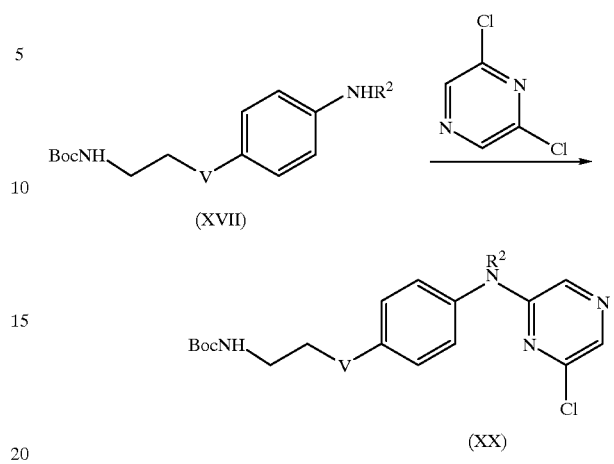

In those cases where the phenyl ring in XVIII is $NHR^2$ and V is a bond then the commercially available 4-(2-aminoethyl)aniline can be employed. When V is oxygen then the following scheme serves to illustrate a route to compounds of the formula (XXI).

Scheme 9

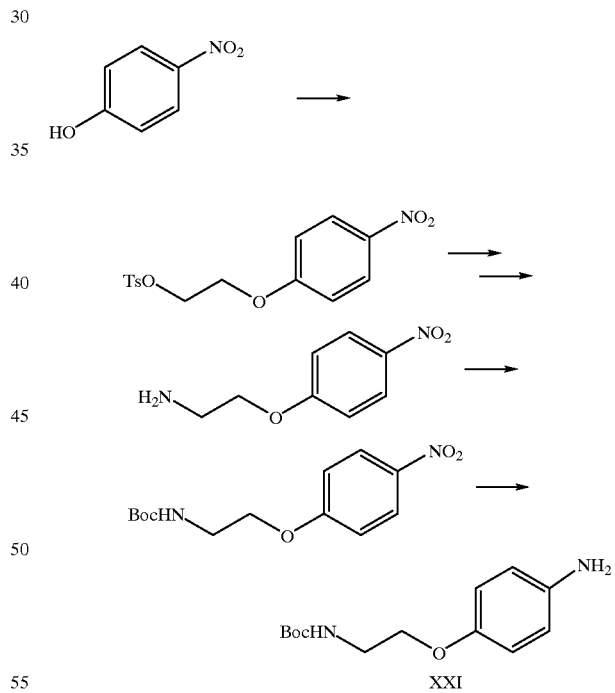

The sodium salt of 4-nitrophenol is alkylated with 1-p-tosylchloroethane, conveniently in refluxing 2-butanone with a base such as potassium carbonate to give the corresponding tosyl derivative as described by N. Ackerley et al., *J. Med. Chem.,* 1995, 38(10), 1608–28. The tosyl group is converted to the amine by treatment with a metal azide such as sodium or lithium azide in an a protic solvent such as dimethylformamide followed by reduction with, for example, triphenylphosine in aqueous tetrahydrofuran as described by H. Staudinger, *Helv. Chim. Acta,* 1919, 2, 635. Protection of the resulting amine, conveniently as the t-butyl carbamate with di-tert-butyl dicarbonate is followed by reduction of the nitro group by, for example, palladium catalyzed hydrogenation to provide the amine (XXI). Aniline (XXI) is thus able to undergo essentially similar transformations as (XVII).

Where the phenyl group of Formula (III) contains an alkylated or acylated nitrogen atom of (XIX) or (XX) reaction of the nitrogen with for example, in the case of acylation, acetic anhydride in pyridine prior to the removal of the benzyl group and reaction of the liberated secondary amine.

Scheme 10

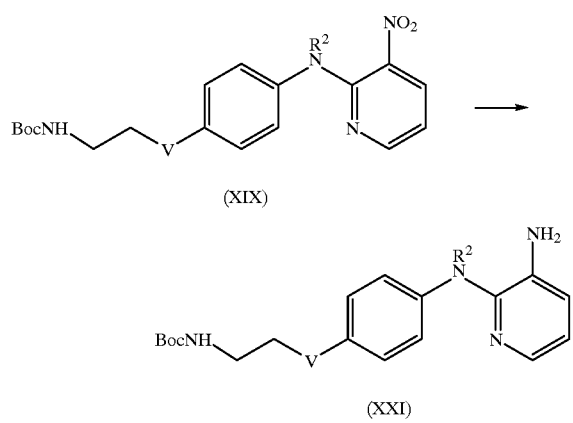

Reduction of the nitro group in compound of Formula (XXI) is conveniently performed by catalytic hydrogenation with palladium on carbon in an inert solvent such as ethanol to provide compounds of Formula (XXI). The newly formed amine ($R_7$ is equal to H) is now able to be reacted in a number of ways known to those skilled in the art.

UREAS:

Scheme 11

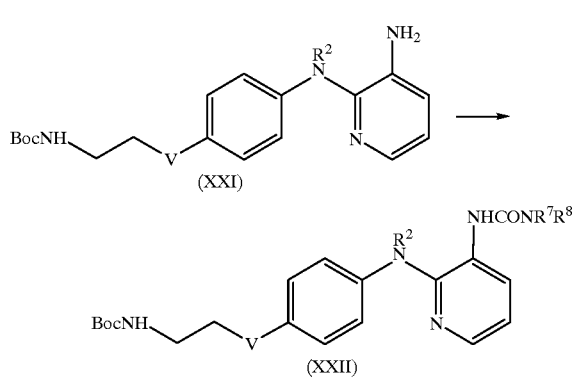

Examples are given below. Thus when a urea group is introduced into Formula (XXI) to provide (XXII) as shown in Scheme 11 compounds of this nature may be prepared under a variety of conditions. Many isocyanates are commercially available and can be conveniently reacted directly with (XXI) in an inert solvent such as tetrahydrofuran to yield the desired ureas. Alternatively, amines can be reacted in the presence of triphosgene and a hindered organic base such as di-isopropylethylamine as described by P. Mayer and R. M. Randad, *J. Org. Chem.,* 1994, 59, 1937. Furthermore, acids can be reacted in a one-pot procedure with diphenylphosphoryl azide and compound (XXI) to yield the desired ureas as described by K. Ninomiya et al *Tetrahedron,* 1974, 30, 2151.

Scheme 12

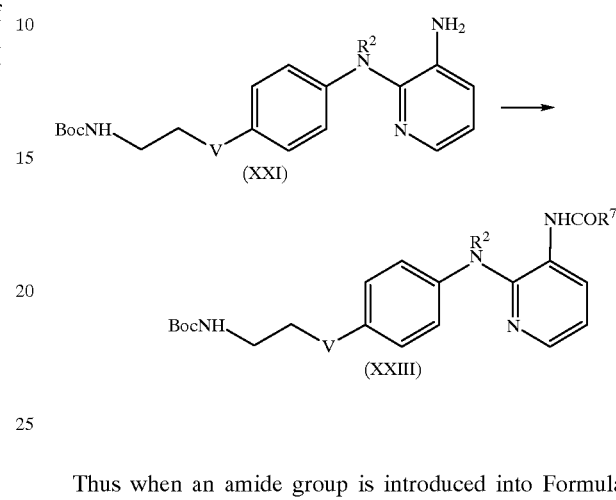

Thus when an amide group is introduced into Formula (XXI) to provide (XXIII) as shown in Scheme 12 then these may be conveniently prepared by reaction of the corresponding acid suitably activated. Many such activating groups may be employed. Such methodology is described in M. Bodansky and A. Bodansky, The Practice of Peptide Synthesis, Springer-Verlag, 1984, 87–150. Many acids are commercially available and can be readily prepared by those skilled in the art. Two most convenient reagents are the water-soluble carbodiimide 1-[3-(dimethylamino)propyl]-3-ethylcarbodiimide hydrochloride typically in an inert solvent such as dichloromethane and the BOP-reagent: benzotriazol-1-yloxy-tris(dimethylamino)phosphonium hexafluorophophate typically in an aprotic solvent such as N,N-dimethylformamide with a tertiary organic base such as triethylamine. Alternatively the acid chloride of the acid may be reacted directly with the amine (XXI) in an inert solvent such as dichloromethane or tetrahyrofuran in the presence of a hindered organic base such as N,N-diisopropylethylamine.

When X is a pyrimidine ring then it may be introduced readily by displacement of a suitable halogen. One such example is illustrated in Scheme 13. Heating compound of Formula (XX) in an excess of the amine readily provides compounds of Formula (XXIV).

Scheme 13

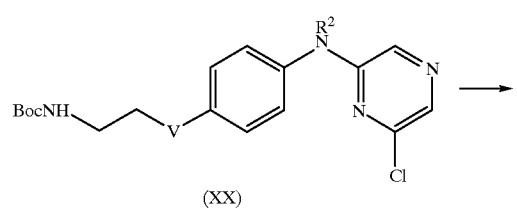

-continued

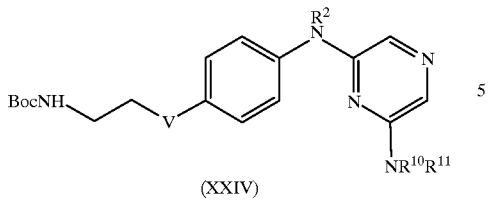

(XXIV)

When $NR^{10}R^{11}$ contains at least one proton then compounds of Formula (XXIV) are transformed as described above for compounds of Formula (XXI).

When the phenyl ring contains an NH there exists a NH group in a suitable 1,2-arrangement on the heterocyclic ring then the possibility of ring closure to form another heterocyclic ring exists. Examples of such imidazoles can be found in K. Hofmann, in *The Chemistry of Heterocyclic Compounds,* A. Weissberger, ed., Interscience Publishers, Inc., New York, 1953.

Compound of Formula (XXV) may be conveniently prepared by a variety of methods familiar to those skilled in the art. Scheme 14 illustrates a typical procedure.

Scheme 14

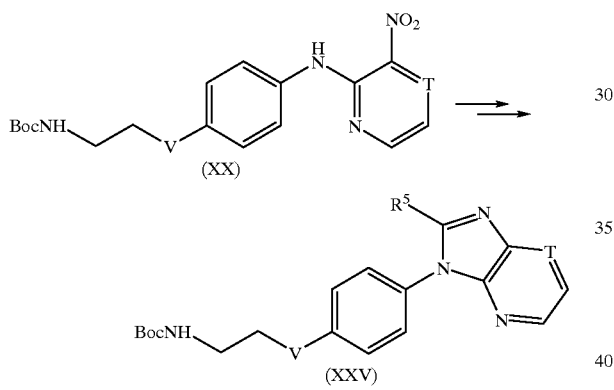

One convenient procedure is the so-called Phillips synthesis described in *The Chemistry of Heterocyclic Compounds,* A. Weissberger, ed., Interscience Publishers, Inc., New York, 1953, 261. Reaction of (XX) with a suitably activated acid to produce an amide as described in M. Bodansky and A. Bodansky, The Practice of Peptide Synthesis, Springer-Verlag, 1984, 87–150 leads to an intermediate nitro-amide that once reduction of the nitro group has been performed as described above can then be conveniently ring closed to provide compounds of Formula (XXV).

In an alternative procedure reduction of the nitro group in (XX) as described above provides compounds of Formula (XXVI) wherein $R^{10}$ and $R^{11}$ are hydrogen Scheme 15

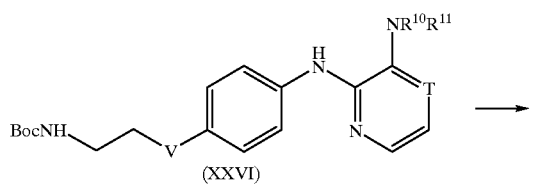

(XXVI)

-continued

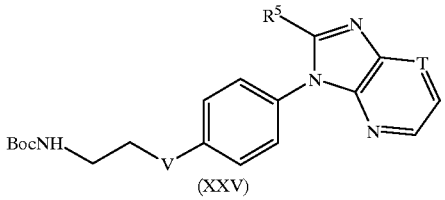

(XXV)

Such compounds may be reacted to produce amides as described above which when heated in an organic base such as pyridine provide a convenient route to compounds of Formula (XXV). Alternatively, compounds of Formula (XXVI) may be treated with an imido ester (R. Roger and D. G. Neilson, *Chem. Rev.,* 1961, 61, 179) in an inert solvent such as ethanol (R. De Selm, *J. Org. Chem.,* 1962, 2163) or chlorobenzene optionally with a hindered organic base such as triethylamine or N,N-diisopropylethylamine to provide compounds of Formula (XXV). In a further method of preparation compounds of Formula (XXVI) are treated with an aldehyde and then with hydrogen and a palladium catalyst in a procedure described by J. S Hinkle and O. W. Lever, Jr. *Tetrahedron,* 1988, 44, 3391.

Scheme 16

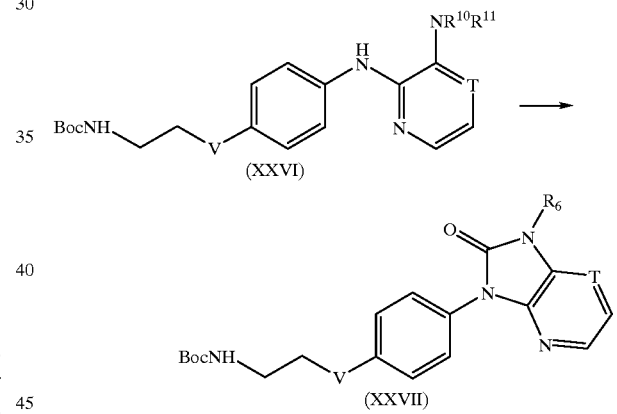

The preparation of imidazopridin-2-ones such as compound of Formula (XXVII) (T=C) as shown in Scheme 16 has been described by M. Israel and L. C. Jones, *J. Het Chem.,* 1969, 6, 735. Wherein condensation of (XXVI) with a keto ester derivative in xylene followed by thermic rearrangement affords compounds of Formula (XXVII). An alternative is to treat (XXVI) with phosgene in toluene followed by heating in acetone (when $R^6=CH(CH_3)_2$).

Scheme 17

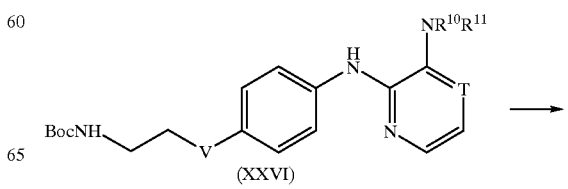

(XXVI)

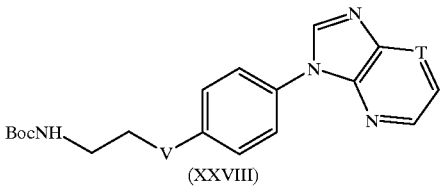

(XXVIII)

The imidazopyridines of formula (XVIII) (with T=C and $R^5$=H) are commonly prepared by treatment of diamino pyridines with a dehydrating agent such as triethylorthoformate under acid catalysis.

Final deprotection of the elaborated protected amines can be conducted using a number of acidic conditions.

When the protecting group is the tert-butyl carbamate one such convenient acid is formic acid. On dissolving the protected tert-butylcarbamate-amines in formic acid with warming removal of the protecting group is smoothly performed.

Reaction with epoxides:

The correspondingly obtained formate salts may be either be utilized with the epoxides of Formula (II) or (IV) to furnish the amino alcohols by reaction in an alcoholic solvent with heat in the presence of a hindered organic base such triethylamine or N,N-diisopropylamine or may be treated with aqueous base to yield the amines free of salt. The desired amino alcohols can thus be obtained by reaction with epoxides (II) or (IV). In those cases where the amine or amine salt is reacted with iodide (XIII) then the procedure described by E. J. Corey and J. O. Link, *J. Org. Chem.*, 1991, 56, 422, namely heated in an anhydrous solvent such as tetrahydrofuran, furnished the desired amino alcohols.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was confirmed with representative compounds of this invention in the following standard pharmacological test procedures, which measured the binding selectivity to the $\beta_1$, $\beta_2$, and $\beta_3$ adrenergic receptors. Binding to the receptors was measured in Chinese Hamster ovary (CHO) cells that were transfected with adrenergic receptors. The following briefly summarizes the procedures used and results obtained.

Transfection of CHO cells with $\beta_1$ and $\beta_2$ adrenergic receptors: CHO cells were transfected with human $\beta_1$- or $\beta_2$-adrenergic receptors as described in Tate, K. M., *Eur. J. Biochem.*, 196:357–361 (1991).

Cloning of Human $\beta_3$-AR Genomic DNA: cDNA was constructed by ligating four polymerase chain reaction (PCR) products using the following primers: an ATG-NarI fragment, sense primer 5'-CTTCCCTACCGCCCCACGCGCGATC3' and anti-sense primer 5'CTGGCGCCCAACGGCCAGTGGC-CAGTC3'; a NarI-AccI fragment, 5'TTGGCGCTGATGGC-CACTGGCCGTTTG3' as sense and 5'GCGCGTAGACGAAGAGCATCACGAG3' as anti-sense primer; an AccI-StyI fragment, sense primer 5'CTCGTGAT-GCTCTTCGTCTCACGCGC3' and anti-sense primer 5'GTGAAGGTGCCCATGATGAGACCCAAGG3' and a StyI-TAG fragment, with sense primer 5'CCCTGTGCAC-CTTGGGTCTCATCATGG3' and anti-sense primer 5'CCTCTGCCCCGGTTACCTACCC3'. The corresponding primer sequences are described in Mantzoros, C. S., et. al., *Diabetes* 45: 909–914 (1996). The four fragments are ligated into a pUC 18 plasmid (Gibco-BRL) and sequenced. Full length $\beta_3$ AR clones (402 amino acids) containing the last 6 amino acids of h$\beta_3$-AR are prepared with the $\beta_3$-$\beta$ARpcDNA3 from ATTC.

Binding Procedure: Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin-Streptompycin and Geneticin. On the day of test procedure, growth medium was replaced with preincubation media (Dulbecco's Modified Eagle Media and incubated for 30 minutes at 37° C. Preincubation medium was replaced with 0.2 ml treatment medium containing DMEM media containing 250 $\mu$M IBMX (isobutyl-1-methylxantine) plus 1 mM ascorbic acid with test compound dissolved in DMSO. Test compounds were tested over a concentration range of $10^{-9}$ M to $10^{-5}$ M for $\beta_3$ cells and $10^{-8}$ to $10^{-4}$ M for $\beta_1$ and $\beta_2$ transfected cells. Isoproterenol ($10^{-5}$ M) was used as an internal standard for comparison of activity. Cells were incubated at 37° C. on a rocker for 30 min with the $\beta_3$ cells and 15 min for $\beta_1$ and $\beta_2$ cells. Incubation was stopped with the addition of 0.2N HCl and neutralized with 2.5N NaOH. The plates, containing the cells and neutralized media, were stored at −20 degrees celsius until ready to test for cAMP using the SPA test kit (Amersham).

Data Analysis and Results: Data collected from the SPA test procedure were analyzed as per cent of the maximal isoproterenol response at $10^{-5}$ M. Activity curves were plotted using the SAS statistical and graphics software. $EC_{50}$ values were generated for each compound and the maximal response (IA) developed for each compound is compared to the maximal response of isoproternol at $10^{-5}$ M from the following formula:

IA=% activity compound/% activity isoproterenol

Table I shows the $\beta$3-adronergic receptor $EC_{50}$ and IA values for the representative compounds of this invention that were evaluated in this standard pharmacological test procedure. These results show that compounds of the present invention have activity at the $\beta$3-adrenergic receptor. The compounds of this invention had weaker or no activity at $\beta$1 and/or $\beta$2-adrenergic receptor.

TABLE I

| Compound No. | $EC_{50}(\beta3, \mu M)$ | IA($\beta$3) |
|---|---|---|
| Example 1 | 0.324 | 0.65 |
| Example 2 | 0.072 | 1.01 |
| Example 3 | 0.095 | 0.76 |
| Example 5 | 0.02 | 1.12 |
| Example 6 | 0.083 | 0.88 |
| Example 7 | 0.057 | 1.12 |
| Example 8 | 0.006 | 1.03 |
| Example 9 | 0.266 | 0.74 |
| Example 10 | 0.006 | 0.96 |
| Example 11 | 0.01 | 0.86 |
| Example 12 | 0.005 | 0.75 |
|  | 0.015 | 0.68 |
| Example 13 | 0.046 | 0.087 |
| Example 14 | 0.054 | 0.086 |

TABLE I-continued

| Compound No. | EC$_{50}$(β3, μM) | IA(β3) |
|---|---|---|
| Example 15 | 0.07 | 1.05 |
| Example 16 | 0.008 | 1 |

Based on the results obtained in these standard pharmacological test procedures, representative compounds of this invention have been shown to be selective β$_3$ adrenergic receptor agonists and are therefore useful in treating metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, the condition, and severity thereof, of the condition being treated, as well as the various physical factors related to the individual being treated. As used in accordance with invention, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum,, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds of the present invention with a sufficient amount of animal feed to provide from about 1 to 1000 ppm of the compound in the feed. Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. The supplement is used as a top dressing for the feed, it likewise helps to ensure uniformity of distribution of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed. The preferred poultry and domestic pet feed usually contain about 0.01 to 400 grams and preferably 10 to 400 grams of active ingredient per ton of feed.

For parenteral administration the compounds of the present invention may be prepared in the form of a paste or a pellet and administered as an implant, usually under the skin of the head or ear of the animal in which increase in lean meat deposition and improvement in lean mean to fat ratio is sought. In general, parenteral administration involves injection of a sufficient amount of the compounds of the present invention to provide the animal with 0.001 to 100 mg/kg/day of body weight of the active ingredient. The preferred dosage for swine, cattle, sheep and goats is in the range of from 0.001 to 50 mg/kg/day of body weight of active ingredient; whereas, the preferred dose level for poultry and domestic pets is usually in the range of from 0.001 to 35 mg/kg/day of body weight.

Paste formulations can be prepared by dispersing the active compounds in a pharmaceutically acceptable oil such as peanut oil, sesame oil, corn oil or the like. Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process. It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body. For the poultry and swine raisers, using the method of the present invention yields leaner animals.

Additionally, the compounds of this invention are useful in increasing the lean mass to fat ratio in domestic pets, for the pet owner or veterinarian who wishes to increase leanness and trim unwanted fat from pet animals, the present invention provides the means by which this can be accomplished.

The following general procedures were used in preparing representative compounds of this invention, and are referred to as applicable.

Procedure A

A mixture of 1 molar equivalent of a hydroxyaryl compound, 1 molar equivalent of (S)-(+)-glycidyl 3-nitrobenzenesulfonate and 1.2 molar equivalent of potassium carbonate in approx. 0.25 molar 2-butanone was heated at reflux for 18 hours. The reaction mixture was cooled and partitioned between ethyl acetate and water. The organic phase was washed with brine and dried over anhydrous magnesium sulfate. The solvent was removed in vacuo and the residue purified by flash chromatography on silica gel Merck-60.

Procedure B

A 0.3 molar solution of the hydroxyaryl compound, R-(+)-glycidol and triphenylphosphine in anhydrous tetrahydrofuran was treated dropwise with 1.1 molar equivalent of diethylazodicarboxylate. After stirring the reaction mixture at ambient temperature overnight, the solvent was removed in vacuo and the residue purified by flash chromatography on silica gel Merck-60.

Procedure C

Triphosgene (0.37 molar equivalent) was dissolved in anhydrous dichloromethane. To this solution, was added dropwise, a mixture of the amine (1 molar equivalent) and N,N-diisopropylethylamine (1.1 molar equivalents) in dichloromethane over 1 hour at ambient temperature. After the addition, a second mixture containing the secondary amine (1 molar equivalent) and anhydrous N,N-diisopropylethylamine (1.1 equivalent) in anhydrous dichloromethane in one portion. In those cases where solubility needs to be increased then anhydrous tetrahydrofuran may be substituted for anhydrous dichloromethane either in part or in total. The reaction was stirred at ambient temperature for 1 hour. The solvent was removed in vacuo and the residue dissolved in a suitable organic solvent and washed with aqueous sodium bicarbonate solution, brine and water. The organic layer was dried with anhydrous sodium (or maganesium) sulfate and evaporated to dryness in vacuo. The residue was purified by flash chromatograhy on silica gel Merck-60 eluting with the specified solvent.

Procedure D

The acid (1 molar equivalent), anhydrous toluene (0.1 M solution) and anhydrous N,N-diisopropylethylamine (1.1 molar equivalents) were combined. To the resulting solution, diphenylphosphoryl azide (1.2 molar equivalents) was added. The reaction was stirred at ambient temperature for 0.5 hour. The reaction was heated to 85° C. for 1 hour. The amine (1 molar equivalent) was added in one portion. The heat was removed, and the reaction was allowed to cool, dichloromethane was added and the organic phases washed with 1N sodium hydroxide, 1N hydrochloric acid, 1N sodium hydroxide, water, brine, and dried with anhydrous sodium (or magnesium) sulfate. The solvent was removed in vacuo and the residue purified by flash chromatograhy on silica gel Merck-60 eluting with the specified solvent.

Procedure E

A mixture of 1 molar equivalent each of the amine and substituted isocyanate was stirred at ambient temperature in dichloromethane or tetrahydrofuran for 1 hour. The reaction mixture was diluted with dichloromethane and washed with 1N hydrochloric acid, water, and brine. The organic layer was dried over anhydrous sodium (or magnesium) sulfate, filtered, and the solvent removed in vacuo. The product was purified by flash chromatography on silica gel Merck-60 eluting with the specified solvent.

Procedure F

The tert-butylcarbamate protected amine was dissolved in formic acid (excess) and stirred at room temperature (heating to 60° C. for 5–10 minutes may also be employed). The formic acid was evaporated under reduced pressure co-evaporating in vacuo with a mixture of chloroform/ethanol achieve a 1:1 formate salt.

Procedure G

The amine (either as the formate salt or as a free base) was dissolved in ethanol with anhydrous N,N-diisopropylethylamine (if the amine salt were employed then: 1.1–1.5 molar equivalents). The reaction mixture was heated at 60° C. overnight. The solvent was removed in vacuo and the residue purified by flash chromatograhy on silica gel Merck-60 eluting with the specified solvent.

Procedure H

The diphenyl-tert-butylsily protected phenol was dissolved in anhydrous tetrahydofuran at ambient temperature and tert-butylammonium fluoride (1 molar equivalent of a 1M tetrahydrofuran solution) was added. The reaction was stirred at ambient temperature for 10–60 minutes. The solvent was removed in vacuo and the residue purified by flash chromatograhy on silica gel Merck-60 eluting with the specified solvent.

The following describes the preparation of intermediates useful in the preparation of the compounds of this invention.

Intermediate 1

(2S)-2-[(4-Benzyloxyphenoxy)methyl]oxirane

4-Benzyloxyphenol (15.00 g, 74.91 mmol) in anhydrous N,N-dimethylformamide (50 mL) was added to a solution of sodium hydride (60% dispersion in oil) (2.88 g, 74.9 mmol) in N,N-dimethylformamide (50 mL). The solution was stirred for 30 minutes and (S)-(+)-glycidyl 4-methylbenzenesulfonate (17.12, 75.0 mmol) was added. The mixture was heated to 80° C. for 2 hours. The solvent was removed and the residue partitioned between diethyl ether and water. The organic phase was washed with brine and dried over anhydrous magnesium sulfate. The solution was filtered and the solvent evaporated to dryness in vacuo. To yield the title compound as a white solid (13.6 g, 53.3 mmol). MS (El, m/z): 256 [M]+

Intermediate 2 tert-Butyl-(4-oxiranylmethoxy-phenoxy)-diphenyl-silane

Step A. (4-Benzyloxy-phenoxy)-tert-butyl-diphenyl-silane

To a solution of imidazole (12.97 g, 190 mmol) and 4-benzyloxy phenol (34.7 g, 173 mmol) in anhydrous dichloromethane (500 mL) was added drop-wise a solution of tert-butyidiphenylchlorosilane (50.0 g, 181 mmol) in dichloromethane (100 mL). The solution was stirred overnight at ambient temperature. The mixture was poured into water (500 mL) and the organic layer washed with saturated sodium hydrogen carbonate, water, brine and dried over anhydrous magnesium sulfate. The solution was filtered and the solvent evaporated to dryness. The solid was crystallized from diethyl ether to provide the title compound (68.9 g, 142 mmol).

MS (El, m/z): 438 [M]+

Mp: 97–98° C.

Anal. Calcd. For $C_{29}H_{30}O_2Si$: C:79.41 H:6.89 Found: C:79.34 H:6.95

Step B. (4-tert-Butyl-diphenyl-silyloxy)-phenol (4-Benzyloxy-phenoxy)-tert-butyl-diphenyl-silane (32.5 g, 67 mmol) was dissolved in ethanol. 10% Palladium on carbon (3.0 g) was added followed by cyclohexene (100 mL). The mixture was heated at reflux for 16 hours. The reaction was cooled to room temperature and filtered through Celite. The solvent was removed in vacuo to yield the title compound (22.0 g, 63 mmol).

MS (El, m/z): 348 [M]+

Step C. tert-Butyl-(4-oxiranylmethoxy-phenoxy)-diphenyl-silane (4-tert-Butyl-diphenyl-silyloxy)-phenol (7.0 g, 20.0 mmol) was reacted according to Procedure B (eluant: 2:1 hexane-diethyl ether) to give the title compound (4.5 g, 11.1 mmol).

Mp: 97–99° C.

Anal. Calcd. For $C_{25}H_{28}O_3Si$: C:74.22 H:6.98 N:0 FOUND: C:74.24 H:6.93 N:0

MS (El, m/z): 404 [M]+

Intermediate 3

4-[(2S)Oxiranylmethoxy]-1,3-dihydro-2H-benzimidazol-2-one

Step A. 2-Nitro-6-[(2S)oxiranylmethoxy]aniline

A mixture of 2-amino-3-nitrophenol (12.0 g, 77.8 mmol), (S)-(+)-glycidyl 3-nitrobenzenesulfonate (20.18, 77.8 mmol) and potassium carbonate (11.8 g, 77.8 mmol) in 2-butanone (100 mL) was heated at reflux for 18 hours essentially as described for Procedure A. The residue was purified by flash chromatography on silica gel Merck-60 (eluant: 2:1 hexane-diethyl ether) to yield the title compound (4.30 g, 20.46 mmol).

Step B. 4-[(2S)Oxiranylmethoxy]-1,3-dihydro-2H-benzimidazol-2-one

2-Nitro-6-[(2S)oxiranylmethoxy]aniline (0.20 g, 0.96 mmol) was dissolved in anhydrous tetrahydrofuran (10 mL). Excess Raney Ni was added and the mixture hydrogenated under an atmosphere of hydrogen overnight. The mixture was filtered through a Celite pad. To the anhydrous tetrahydrofuran solution was added with cooling anhydrous N,N-diisopropylethylamine (0.365 mL) followed by phosgene in toluene (0.525 mL). The solvent was partially removed and the title compound collected by filtration (0.10 g, 0.49 mmol).

MS ((+)ESI, m/z): 207 [M+H]+

The following describe the preparation of representative examples of this invention.

EXAMPLE 1

4-((2S)-2-Hydroxy-3-{2-[4-(3-nitro-pyridin-2-ylamino)-phenyl]-ethylamino}-propoxy)-phenol Step A. tert-Butyl 4-[(3-nitro-2-pyridinyl)amino]phenethylcarbamate 2-Chloro-3-nitropyridine (3.63 g, 22.9 mmol), tert-butyl 4-aminophenethylcarbamate (5.41 g, 22.9 mmol) and N,N-diisopropylethylamine (5.62 mL, 32.2 mmol) were combined in anhydrous N,N-dimethylformamide (50 mL) and heated at 100° C. for 18 hours. The solvent was removed in vacuo and the residue dissolved in ethyl acetate and washed with water, 1N hydrochloric acid and brine. The solution was dried over anhydrous magnesium sulfate, filtered and the solvent removed in vacuo to yield a dark solid (7.64 g, 21.32 mmol).

MS (El, m/z): 358 [M]+

Step B. N-[4-(2-Aminoethyl)phenyl]-3-nitro-2-pyridinamine tert-Butyl 4-[(3-nitro-2-pyridinyl)amino]phenethylcarbamate (3.0 g, 8.37 mmol) was reacted according to Procedure F to provide the title compound as the formate salt. The solid was dissolved in chloroform and 1N sodium hydroxide added. The organic phase was separated and washed with brine and dried over anhydrous magnesium sulfate. The solution was filtered and the solvent removed in vacuo to yield the title compound as a dark solid (2.0 g, 7.74 mmol) which was used without further purification.

MS ((+)ESI, m/z): 259 [M+H]+

Step C. (2S)-1-(4-{[tert-Butyl(diphenyl)silyl]oxy}phenoxy)-3-({4-[(3-nitro-2-pyridinyl)amino]phenethyl}amino)-2-propanol N-[4-(2-Aminoethyl)phenyl]-3-nitro-2-pyridinamine (0.87 g, 3.37 mmol) was reacted with tert-butyl-(4-oxiranylmethoxy-phenoxy)-diphenyl-silane (1.36 g, 3.36 mmol) according to Procedure G (eluant: 20:1 going to 5:1 chloroform-methanol) to give the title compound (0.59 g, 0.21 mmol).

Step D. 4-((2S)-2-Hydroxy-3-{2-[4-(3-nitro-pyridin-2-ylamino)-phenyl]-ethylamino}-propoxy)-phenol (2S)-1-(4-{[tert-Butyl(diphenyl)silyl]oxy}phenoxy)-3-({4-[(3-nitro-2-pyridinyl)amino]phenethyl}amino)-2-propanol (0.06 g, 0.09 mmol) was reacted according to Procedure H (eluant: 10:1 going to 5:1 chloroform) to give the title compound (0.03 g, 0.07 mmol).

MS ((−)ESI, m/z): 259 [M−H]−

Anal. Calcd. For $C_{22}H_{24}N_4O_5$+1.33 $H_2O$: C:58.93 H:5.99 N 12.49 Found: C:59.08 H:5.65 N:12.19

Mp: 148–149° C.

EXAMPLE 2

4-((2R)-3-{2-[4-(3-Amino-pyridin-2-ylamino)-phenyl]-ethylamino}-2-hydroxy-propoxy)-phenol (2S)-1-(4-{[tert-Butyl(diphenyl)silyl]oxy}phenoxy)-3-({4-[(3-nitro-2-pyridinyl)amino]phenethyl}amino)-2-propanol (0.36 g, 0.543 mmol) was dissolved in ethanol, catalytic 10% palladium on carbon added, and shaken on a Parr apparatus under 50 psi hydrogen for 2 hours. The catalyst was removed by filtration through Celite and the filtrate taken to dryness in vacuo. The residue was dissolved in anhydrous tetrahydrofuran and treated with tert-butylammonium fluoride (0.7 mL, 1M solution in tetrahydrofuran, 0.7 mmol). The reaction was stirred at ambient temperature for 5 minutes, the solvent removed in vacuo and the residue purified by flash chromatography on silica gel Merck-60 (eluant: 20:1 going to 5:1 chloroform-methanol containing 2% triethylamine). The solvent was removed in vacuo to furnish the title compound (0.05 g, 0.127 mmol).

MS ((+) ESI, m/z): 395 [M+H]+

Anal. Calcd. For $C_{22}H_{26}N_4O_3$+0.75 $H_2O$: C:64.77 H:6.79 N:13.73 Found: C:64.89 H:6.92 N:13.35

Mp: 63–65° C.

EXAMPLE 3

4-{(2S)-2-Hydroxy-3-[2-(4-imidazo[4,5-b]pyridin-3-yl-phenyl)-ethylamino]-propoxy}-phenol (2S)-1-(4-{[tert-Butyl(diphenyl)silyl]oxy}phenoxy)-3-({4-[(3-nitro-2-pyridinyl) amino]phenethyl}amino)-2-propanol (0.523 g, 0.79 mmol) was dissolved in anhydrous tetrahydrofuran at 0° C., di-tert-butyl dicarbonate (0.172 g, 0.79 mmol) was added and the reaction placed in the refrigerator for 48 hours. The solvent was removed in vacuo and the residue dissolved in ethanol, catalytic 10% palladium on carbon added, and shaken on a Parr apparatus under 50 psi hydrogen. The catalyst was removed by filtration through Celite and the filtrate taken to dryness in vacuo. The residue was dissolved in formic acid and stirred at ambient temperature overnight. The solvent was removed in vacuo and the residue purified by flash chromatography on silica gel Merck-60 (eluant: 20:1 going to 5:1 chloroform-methanol). The solvent was removed in vacuo to furnish the title compound (0.17 g, 0.42 mmol).

MS ((+)ESI, m/z): 405 [M+H]+, 809 [2M+H]+

Anal. Calcd. For $C_{23}H_{24}N_4O_3$+1.33 $H_2O$+0.20 $C_6H_{15}N$: C:64.63 H:6.87 N:13.08 Found C: 64.41 H:6.49 N:13.01

Mp: 49–52° c.

EXAMPLE 4

1-Hexyl-3-[2-(4-{2-[(2S)-2-hydroxy-3-(4-hydroxy-phenoxy)-propylamino]-ethyl}-phenylamino)-pyridin-3-yl]-urea Step A. tert-Butyl 4-[(3-amino-2-pyridinyl)amino]phenethylcarbamate tert-Butyl 4-[(3-nitro-2-pyridinyl)amino]phenethylcarbamate (2.7 g, 7.53 mmol) was dissolved in ethanol (70 mL), catalytic 10% palladium on carbon added, and shaken on a Parr apparatus under 50 psi hydrogen overnight. The catalyst was removed by filtration through Celite and the filtrate taken to dryness in vacuo. The residue was purified by flash chromatography on silica gel Merck-60 (eluant: 1:1 ethyl acetate-hexane) to yield the title compound.

MS ((+)ESI, m/z): 329 [M+H]+, 657 [2M+H]+

Step B. tert-Butyl 4-[(3-{[(hexylamino)carbonyl]amino}-2-pyridinyl)amino]phenethylcarbamate tert-Butyl 4-[(3-amino-2-pyridinyl)amino]phenethylcarbamate (0.30 g, 0.914 mmol) was reacted with hexyl isocyanate (0.14 g, 1.1 mmol) according to Procedure E overnight at reflux in dichloromethane. The title compound was crystallized from ethyl acetate/hexane (0.32 g, 0.70 mmol).

MS ((+)ESI, m/z): 456 [M+H]+

Step C. N-{2-[4-(2-Aminoethyl)anilino]-3-pyridinyl}-N'-hexylurea Formate tert-Butyl 4-[(3-{[(hexylamino)carbonyl]amino}-2-pyridinyl)amino]phenethyl carbamate (0.32 g, 0.70 mmol) was reacted according to Procedure F to provide the title compound (0.24 g, 0.60 mmol) which was used without further purification.

Step D. N-{2-[4-(2-{[(2S)-3-(4-{[tert-butyl(diphenyl)silyl]oxy}phenoxy)-2-hydroxypropyl]amino}ethyl)anilino]-3-pyridinyl}-N'-hexylurea N-{2-[4-(2-Aminoethyl)anilino]-3-pyridinyl}-N'-hexylurea formate (0.24 g, 0.60 mmol) was reacted with tert-butyl-(4-oxiranylmethoxy-phenoxy)-diphenyl-silane (0.242 g, 0.60 mmol) according to Procedure G (eluant: 20:1 going to 10:1 chloroform-methanol) to give the title compound (0.15 g, 0.197 mmol).

Step E. 1-Hexyl-3-[2-(4-{2-[(2S)-2-hydroxy-3-(4-hydroxy-phenoxy)-propylamino]-ethyl}-phenylamino)-pyridin-3-yl]-urea N-{2-[4-(2-{[(2S)-3-(4-{[tert-Butyl(diphenyl)silyl]oxy}phenoxy)-2-hydroxypropyl]amino}ethyl)anilino]-3-pyridinyl}-N'-hexylurea (0.15 g, 0.197 mmol) was reacted according to Procedure H (eluant: 10:1 going to 5:1 chloroform-methanol containing 2% triethylamine) to give the title compound (0.09 g, 0.173 mmol).

MS ((+)ESI, m/z): 522 [M+H]+

Anal. Calcd. For $C_{29}H_{39}N_5O_4$+1.00 HCl: C:62.41 H:7.22 N:12.55 Found: C:62.13 H:7.1 1 N:12.2

Mp: 61–64° C.

EXAMPLE 6

N-[2-(4-{2-[(2S)-2-Hydroxy-3-(4-hydroxy-phenoxy)-propylamino]-ethyl}-phenylamino)-pyridin-3-yl]-benzamide Step A. tert-Butyl 4-{[3-(benzoylamino)-2-pyridinyl]amino}phenethylcarbamate tert-Butyl 4-[(3-amino-2-pyridinyl)amino]phenethylcarbamate (0.33 g, 1.0 mmol) was dissolved in anhydrous pyridine (2 mL) and benzoyl chloride (0.117 mL, 1.0 mmol) added. The reaction was heated at 90° C. for 1 hour. The solvent was removed and the residue co-evaporated with toluene to obtain a solid which was purified by flash chromatography on silica gel Merck-60 (eluant: 50:1 going to 20:1 chloroform:methanol) to yield the title compound (0.15 g, 0.347 mmol).

MS ((+)ESI, m/z): 433 [M+H]+

Step B. N-{2-[4-(2-Aminoethyl)anilino]-3-pyridinyl}benzamide tert-Butyl 4-{[3-(benzoylamino)-2-pyridinyl]amino}phenethylcarbamate (0.15 g, 0.347 mmol) was reacted according to Procedure F to provide the title compound as the formate salt. The solid was dissolved in chloroform and 1N sodium hydroxide. The organic phase was separated and washed with brine and dried over anhydrous magnesium sulfate. The solution was filtered and the solvent removed in vacuo to yield the title compound (0.1 g, 0.30 mmol) which was used without further purification.

Step C. N-{2-[4-(2-{[(2S)-3-(4-{[tert-Butyl(diphenyl)silyl]oxy}phenoxy)-2-hydroxypropyl]amino}ethyl)anilino]-3-pyridinyl}benzamide N-{2-[4-(2-Aminoethyl)anilino]-3-pyridinyl}benzamide (0.1 g, 0.30 mmol) was reacted with tert-butyl-(4-oxiranylmethoxy-phenoxy)-diphenyl-silane (0.107 g, 0.265 mmol) according to Procedure G (eluant: 20:1 going to 10:1 chloroform-methanol) to give the title compound (0.064 g, 0.087 mmol).

Step D. N-[2-(4-{2-[(2S)-2-Hydroxy-3-(4-hydroxy-phenoxy)-propylamino]-ethyl}-phenylamino)-pyridin-3-yl]-benzamide N-{2-[4-(2-{[(2S)-3-(4-{[tert-Butyl(diphenyl)silyl]oxy}phenoxy)-2-hydroxypropyl]amino}ethyl)anilino]-3-pyridinyl}benzamide (0.064 g, 0.087 mmol) was reacted according to Procedure H (eluant: 10:1 going to 5:1 chloroform-methanol containing 2% triethylamine) to give the title compound (0.039 g, 0.078 mmol).

Mp: 97–99° C.

MS ((+)ESI, m/z): 499 [M+H]+

Anal. Calcd. For $C_{29}H_{30}N_4O_4+1.00$ HCl+1.00 $H_2O$: C:62.98 H:6.01 N:10.13 Found: C:62.82 H:5.67 N:9.74

EXAMPLE 7

3-(4-{2-[(2S)-2-Hydroxy-3-(4-hydroxy-phenoxy)-propylamino]-ethyl}-phenyl)-1-isopropenyl-1,3-dihydro-imidazo[4,5-b]pyridin-2-one Step A. tert-Butyl 4-(1-isopropenyl-2-oxo-1,2-dihydro-3H-imidazo[4,5-b]pyridin-3-yl)phenethylcarbamate tert-Butyl 4-[(3-amino-2-pyridinyl)amino]phenethylcarbamate (1.0 g, 3.05 mmol) was dissolved in anhydrous dichloromethane. To this solution was added anhydrous N,N-diisopropylethylamine (1.17 mL, 6.7 mmol) and phosgene (1.76 mL, 1.9 M solution in toluene, 3.3 mmol). The reaction was stirred at ambient temperature for 10 minutes, a further portion of phosgene added and the reaction stirred for a further 40 minutes. The reaction was diluted with dichloromethane and washed with 1N sodium hydroxide and brine, dried over anhydrous magnesium sulfate and filtered. The solution was taken to dryness in vacuo and the residue was purified by flash chromatography on silica gel Merck-60 (eluant:1:1 ethyl acetate-hexane) to yield a solid which was crystallized from acetone (0.38 g, 0.963 mmol).

MS ((+)ESI, m/z): 395 [M+H]+

Step B. 3-[4-(2-Aminoethyl)phenyl]-1-isopropenyl-1,3-dihydro-2H-imidazo[4,5-b]pyridin-2-one Formate tert-Butyl 4-(1-isopropenyl-2-oxo-1,2-dihydro-3H-imidazo[4,5-b]pyridin-3-yl)phenethylcarbamate (0.38 g, 0.963 mmol) was reacted according to Procedure F to provide the title compound (0.32 g, 0.96 mmol).

Step C. 3-[4-(2-{[(2S)-3-(4-{[tert-Butyl(diphenyl)silyl]oxy}phenoxy)-2-hydroxypropyl]amino}ethyl)phenyl]-1-isopropenyl-1,3-dihydro-2H-imidazo[4,5-b]pyridin-2-one 3-[4-(2-Aminoethyl)phenyl]-1-isopropenyl-1,3-dihydro-2H-imidazo[4,5-b]pyridin-2-one formate (0.32 g, 0.96 mmol) was reacted with tert-butyl-(4-oxiranylmethoxy-phenoxy)-diphenyl-silane (0.433 g, 1.07 mmol) according to Procedure G (eluant: 20:1 going to 10:1 chloroform-methanol) to give the title compound (0.19 g, 0.272 mmol).

Step D. 3-(4-{2-[(2S)-2-Hydroxy-3-(4-hydroxy-phenoxy)-propylamino]-ethyl}-phenyl)-1-isopropenyl-1,3-dihydro-imidazo[4,5-b]pyridin-2-one 3-[4-(2-{[(2S)-3-(4-{[tert-Butyl(diphenyl)silyl]oxy}phenoxy)-2-hydroxypropyl]amino}ethyl)phenyl]-1-isopropenyl-1,3-dihydro-2H-imidazo[4,5-b]pyridin-2-one (0.19 g, 0.272 mmol) was reacted according to Procedure H (eluant: 10:1 going to 5:1 chloroform-methanol containing 2% triethylamine) to give the title compound (0.108 g, 0.234 mmol).

Mp: 62–64° C.

MS ((+)ESI, m/z): 461 [M+H]+

Anal. Calcd. For $C_{26}H_{28}N_4O_4+1.25$ $H_2O+0.10$ $CHCl_3$: C:63.33 H:6.23 N:11.32 Found: C:63.76 H:5.9 N:10.93

EXAMPLE 8

4-[(2S)-3-(2-{4-[2-(4-Ethyl-phenyl)-imidazo[4,5-b]pyridin-3-yl]-phenyl}-ethylamino)-2-hydroxy-propoxy]-phenol Step A. Methyl 4-ethylbenzenecarboximidoate Hydrodrochloride Hydrogen chloride gas was bubbled through a methanol solution of 4-ethylbenzonitrile (5.0 g, 38.11 mmol) at 0° C. for 30 minutes. The reaction was sealed and stood at ambient temperature overnight. The solvent was removed in vacuo and the oily residue triturated with diethyl ether. The resulting solid was removed to yield the title compound which was stored in a dry atmosphere.

Step B. tert-Butyl 4-[2-(4-ethylphenyl)-3H-imidazo[4,5-b]pyridin-3-yl]phenethylcarbamate To a solution of anhydrous N,N-diisopropylethylamine (0.4 mL, 2.29 mmol) and methyl 4-ethylbenzenecarboximidoate hydrodrochloride (0.30 g, 1.5 mmol) in chlorobenzene (30 mL) was added tert-butyl 4-[(3-amino-2-pyridinyl)amino]phenethylcarbamate (0.333 g, 1.01 mmol). The reaction was heated at 90° C. for 36 hours. The solvent was removed in vacuo and the residue combined with a similar residue obtained in an analogous repeat reaction and purified together by flash chromatography on silica gel Merck-60 (eluant 50:1 chloroform-methanol) to yield the title compound (0.33 g, 0.746 mmol).

MS ((+)ESI, m/z): 443 [M+H]+

Step C. 2-{4-[2-(4-ethylphenyl)-3H-imidazo[4,5-b]pyridin-3-yl]phenyl}-1-ethanamine Formate tert-Butyl 4-[2-(4-ethylphenyl)-3H-imidazo[4,5-b]pyridin-3-yl]phenethylcarbamate (0.33 g, 0.746 mmol) was reacted according to Procedure F to provide the title compound (0.27 g, 0.746 mmol).

Step D. (2S)-1-(4-{[tert-butyl(diphenyl)silyl]oxy}phenoxy)-3-({4-[2-(4-ethylphenyl)-3H-imidazo[4,5-b]pyridin-3-yl]phenethyl}amino)-2-propanol 2-{4-[2-(4-Ethylphenyl)-3H-imidazo[4,5-b]pyridin-3-yl]phenyl}-1-ethanamine formate (0.27 g, 0.746 mmol) was reacted with tert-butyl-(4-oxiranylmethoxy-phenoxy)-diphenyl-silane (0.2 g, 0.5 mmol) according to Procedure G (eluant: 20:1 going to 5:1 chloroform-methanol) to give the title compound (0.13 g, 0.174 mmol).

Step E. 4-[(2S)-3-(2-{4-[2-(4-Ethyl-phenyl)-imidazo[4,5-b]pyridin-3-yl]-phenyl}-ethylamino)-2-hydroxy-propoxy]-phenol (2S)-1-(4-{[tert-butyl(diphenyl)silyl]oxy}phenoxy)-3-({4-[2-(4-ethylphenyl)-3H-imidazo[4,5-b]pyridin-3-yl]phenethyl}amino)-2-propanol (0.13 g, 0.174 mmol) was reacted according to Procedure H (eluant: 10:1 going to 5:1 chloroform-methanol containing 2% triethylamine) to give the title compound (0.074 g, 0.146 mmol).

Mp: 75–78° C.

MS ((+)ESI, m/z): 509 [M+H]$^+$

Anal. Calcd. For $C_{31}H_{32}N_4O_3$+1.00 HCl+0.25 $H_2O$: C:67.75 H:6.14 N:10.19 Found: C:67.82 H:6.56 N:9.7

EXAMPLE 9

4-((2S)-2-Hydroxy-3-{2-[4-(2-pentyl-imidazo[4,5-b]pyridin-3-yl)-phenyl]-ethylaminol}-propoxy)-phenol Step A. tert-Butyl 4-(2-pentyl-3H-imidazo[4,5-b]pyridin-3-yl)phenethylcarbamate tert-Butyl 4-[(3-amino-2-pyridinyl)amino]phenethylcarbamate (1.75 g, 5.33 mmol) was dissolved in anhydrous pyridine (30 mL) and hexanoyl chloride (0.825 g, 6.13 mmol) added. The reaction was heated at 100° C. for 18 hours. The solvent was removed and the residue partitioned between water and chloroform. The organic phase was washed with water and brine, dried over anhydrous magnesium sulfate and filtered. The solution was taken to dryness in vacuo and the residue purified by flash chromatography on silica gel Merck-60 (eluant 20:1 chloroform-methanol followed by 1:1 ethyl acetate-hexane) to yield the title compound (0.87 g, 2.13 mmol).

Step B. 2-[4-(2-Pentyl-3H-imidazo[4,5-b]pyridin-3-yl)phenyl]-1-ethanamine tert-Butyl 4-(2-Pentyl-3H-imidazo[4,5-b]pyridin-3-yl)phenethylcarbamate (0.87 g, 2.13 mmol) was reacted according to Procedure F to provide the title compound as the formate salt. The solid was dissolved in chloroform and washed with 1N sodium hydroxide. The organic phase was separated and washed with brine and dried over anhydrous magnesium sulfate. The solution was filtered and the solvent removed in vacuo to yield the title compound which was used without further purification.

Step C. (2S)-1-(4-{[tert-Butyl(diphenyl)silyl]oxy}phenoxy)-3-{[4-(2-pentyl-3H-imidazo[4,5-b]pyridin-3-yl)phenethyl]amino}-2-propanol 2-[4-(2-Pentyl-3H-imidazo[4,5-b]pyridin-3-yl)phenyl]-1-ethanamine (0.231 g, 0.652 mmol) was reacted with tert-butyl-(4-oxiranylmethoxy-phenoxy)-diphenyl-silane (0.302 g, 0.748 mmol) according to Procedure G (eluant: 20:1 going to 5:1 chloroform-methanol) to give the title compound (0.20 g, 0.281 mmol).

Step D. 4-((2S)-2-Hydroxy-3-{2-[4-(2-pentyl-imidazo[4,5-b]pyridin-3-yl)-phenyl]-ethylamino}-propoxy)-phenol (2S)-1-(4-{[tert-Butyl(diphenyl)silyl]oxy}phenoxy)-3-{[4-(2-pentyl-3H-imidazo[4,5-b]pyridin-3-yl)phenethyl]amino}-2-propanol (0.20 g, 0.281 mmol) was reacted according to Procedure H (eluant: 10:1 going to 5:1 chloroform-methanol containing 1% ammonium hydroxide) to give the title compound (0.123 g, 0.259 mmol).

Mp: 50–52° C.

MS ((+)ESI, m/z): 475 [M+H]$^+$

Anal. Calcd. For $C_{28}H_{34}N_4O_3$+0.50 $H_2O$: C:69.54 H:7.29 N:11.58 Found: C:69.88 N:7.23 H:11.53

EXAMPLE 10

4-[(2S)-3-(2-{4-[2-(4-Cyclohexyl-phenyl)-imidazo[4,5-b]pyridin-3-yl]-phenyl}-ethylamino)-2-hydroxy-propoxy]-phenol Step A tert-Butyl 4-[2-(4-cyclohexylphenyl)-3H-imidazo[4,5-b]pyridin-3-yl]phenethylcarbamate tert-Butyl 4-[(3-amino-2-pyridinyl)amino]phenethylcarbamate (1.4 g, 4.26 mmol) was dissolved in anhydrous pyridine and 4-cyclohexylbenzoyl chloride (prepared and used crude following solvent removal from 4-cyclohexylbenzoic acid (0.958 g, 0.469 mmol), oxalyl chloride (0.430 g, 4.93 mmol) and N,N-diimethylformamide (0.011 mL) in anhydrous dichloromethane/tetrahydrofuran (50 mL)) added. The reaction was heated at 100° C. for 18 hours. The solvent was removed and the residue partitioned between water and chloroform. The organic phase was washed with water and brine, dried over anhydrous magnesium sulfate and filtered. The solution was taken to dryness in vacuo and the residue purified by flash chromatography on silica gel Merck-60 (eluant 20:1 chloroform-methanol followed by 1:1 ethyl acetate-hexane) to yield the title compound (0.95 g, 1.92 mmol).

MS ((+)ESI, m/z): 497 [M+H]$^+$

Step B. 4-[2-(4-Cyclohexylphenyl)-3H-imidazo[4,5-b]pyridin-3-yl]phenethylamine tert-Butyl 4-[2-(4-cyclohexylphenyl)-3H-imidazo[4,5-b]pyridin-3-yl]phenethyl carbamate (0.95 g, 1.92 mmol) was reacted according to Procedure F to provide the title compound as the formate salt. The solid was dissolved in chloroform and washed with 1N sodium hydroxide. The organic phase was separated and washed with brine and dried over anhydrous magnesium sulfate. The solution was filtered and the solvent removed in vacuo to yield the title compound (0.37 g, 0.93 mmol) which was used without further purification.

Step C. (2S)-1-(4-{[tert-Butyl(diphenyl)silyl]oxy}phenoxy)-3-({4-[2-(4-cyclohexylphenyl)-3H-imidazo[4,5-b]pyridin-3-yl]phenethyl}amino)-2-propanol 4-[2-(4-Cyclohexylphenyl)-3H-imidazo[4,5-b]pyridin-3-yl]phenethylamine (0.37 g, 0.93 mmol) was reacted with tert-butyl-(4-oxiranylmethoxy-phenoxy)-diphenyl-silane (0.377 g, 0.93 mmol) according to Procedure G (eluant: 20:1 going to 5:1 chloroform-methanol) to give the title compound (0.317 g, 0.396 mmol).

Step D. 4-[(2S)-3-(2-{4-[2-(4-Cyclohexyl-phenyl)-imidazo[4,5-b]pyridin-3-yl]-phenyl}-ethylamino)-2-hydroxy-propoxy]-phenol (2S)-1-(4-{[tert-Butyl(diphenyl)silyl]oxy}phenoxy)-3-({4-[2-(4-cyclohexylphenyl)-3H-imidazo[4,5-b]pyridin-3-yl]phenethyl}amino)-2-propanol (0.317 g, 0.396 mmol) was reacted according to Procedure H (eluant: 10:1 going to 5:1 chloroform-methanol containing 1% ammonium hydroxide) to give the title compound (0.21 g, 0.37 mmol).

Mp: 100–102° C.

MS ((+)ESI, m/z): 563 [M+H]$^+$

Anal. Calcd. For $C_{35}H_{38}N_4O_3$+1.50 $H_2O$: C:71.28 H:7.07 N:9.50 Found: C:71.20 H:6.70 N:9.16

EXAMPLE 11

4-[(2S)-3-(2-{4-[2-(2-Cyclopentyl-ethyl)-imidazo[4,5-b]pyridin-3-yl]-phenyl}-ethylamino)-2-hydroxy-propoxy]-phenol Step A. tert-Butyl 4-[2-(2-cyclopentylethyl)-3H-imidazo[4,5-b]pyridin-3-yl]phenethylcarbamate tert-Butyl 4-[(3-amino-2-pyridinyl)amino]phenethylcarbamate (1.0 g, 3.05 mmol) was dissolved in anhydrous pyridine and 3-cyclopentylpropanoyl chloride (0.489 g, 3.04 mmol) added. The reaction was heated at 100° C. for 18 hours. The solvent was removed and the residue partitioned between water and chloroform. The organic phase was washed with water and brine, dried over anhydrous magnesium sulfate and filtered. The solution was taken to dryness in vacuo and the residue purified by flash chromatography on silica gel Merck-60 (eluant 20:1 chloroform-methanol followed by 1:1 ethyl acetate-hexane) to yield the title compound (0.93 g, 2.14 mmol).
Step B. 4-[2-(2-Cyclopentylethyl)-3H-imidazo[4,5-b]pyridin-3-yl]phenethylamine tert-Butyl 4-[2-(2-cyclopentylethyl)-3H-imidazo[4,5-b]pyridin-3-yl]phenethyl carbamate (0.93 g, 2.14 mmol) was reacted according to Procedure F to provide the title compound as the formate salt. The solid was dissolved in chloroform and washed with 1N sodium hydroxide. The organic phase was separated and washed with brine and dried over anhydrous magnesium sulfate. The solution was filtered and the solvent removed in vacuo to yield the title compound which was used without further purification.

MS ((+)ESI, m/z): 335 [M+H]$^+$

Step C. (2S)-1-(4-{[tert-butyl(diphenyl)silyl]oxy}phenoxy)-3-({4-[2-(2-cyclopentylethyl)-3H-imidazo[4,5-b]pyridin-3-yl]phenethyl}amino)-2-propanol 4-[2-(2-Cyclopentylethyl)-3H-imidazo[4,5-b]pyridin-3-yl]phenethylamine (0.22 g, 0.658 mmol) was reacted with tert-butyl-(4-oxiranylmethoxy-phenoxy)-diphenyl-silane (0.266 g, 0.656 mmol) according to Procedure G (eluant: 20:1 going to 5:1 chloroform-methanol) to give the title compound (0.209 g, 0.283 mmol).

Step D. 4-[(2S)-3-(2-{4-[2-(2-Cyclopentyl-ethyl)-imidazo[4,5-b]pyridin-3-yl]-phenyl}-ethylamino)-2-hydroxy-propoxy]-phenol (2S)-1-(4-{[tert-butyl(diphenyl)silyl]oxy}phenoxy)-3-({4-[2-(2-cyclopentylethyl)-3H-imidazo[4,5-b]pyridin-3-yl]phenethyl}amino)-2-propanol (0.209 g, 0.283 mmol) was reacted according to Procedure H (eluant: 10:1 going to 5:1 chloroform-methanol containing 1% ammonium hydroxide) to give the title compound (0.11 g, 0.22 mmol).
Mp: 59–61° C.

MS ((+)ESI, m/z): 501 [M+H]$^+$

Anal. Calcd. For $C_{30}H_{36}N_4O_3+0.50 H_2O$: C:70.70 H:7.32 N:10.99 Found: C:70.41 H:7.18 N:10.74

EXAMPLE 12

4-[3-(2-{4-[2-(2-Cyclopentyl-ethyl)-imidazo[4,5-b]pyridin-3-yl]-phenyl}-ethylamino) -2-hydroxy-propoxy]-1,3-dihydro-benzoimidazol-2-one 4-[2-(2-Cyclopentylethyl)-3H-imidazo[4,5-b]pyridin-3-yl]phenethylamine (0.229 g, 0.68 mmol) was reacted with 4-[(2S)oxiranylmethoxy]-1,3-dihydro-2H-benzimidazol-2-one (0.141 g, 0.68 mmol) according to Procedure G (eluant: 20:1 going to 5:1 chloroform-methanol containing 1% ammonium hydroxide) to give the title compound (0.032 g, 0.059 mmol).

Mp: 115–117° C.

MS ((+)ESI, m/z): 541 [M+H]$^+$

Anal. Calcd. For $C_{31}H_{36}N_6O_3+1.00$ HCl: C:64.52 H:6.46 N:14.56 Found: C:64.33 H:6.42 N:14.22

EXAMPLE 13

4-((2S)-2-Hydroxy-3-{2-[4-(2-pentyl-imidazo[4,5-b]pyridin-3-yl)-phenyl]-ethylaminol}-propoxy)-1,3-dihydro-benzoimidazol-2-one tert-Butyl 4-(2-pentyl-3H-imidazo[4,5-b]pyridin-3-yl)phenethylcarbamate (0.195 g, 0.632 mmol) was reacted with 4-[(2S)oxiranylmethoxy]-1,3-dihydro-2H-benzimidazol-2-one (0.131 g, 0.635 mmol) according to Procedure G (eluant: 20:1 going to 5:1 chloroform-methanol containing 1% ammonium hydroxide) to give the title compound (0.015 g, 0.032 mmol).

MS ((+)ESI, m/z): 515 [M+H]$^+$

Anal. Calcd. For $C_{29}H_{34}N_6O_3+1.00 H_2O+0.15 C_4H_{10}O$: C:65.38 H:6.95 N:15.46 Found: C:65.6 H:6.6 N:15.15

EXAMPLE 14

4-{3-[2-(4-{2-[2-Chloro-4-(3-methyl-pyrazol-1-yl)-phenyl]-imidazo[4,5-b]pyridin-3-yl}-phenyl)-ethylamino]-2-hydroxy-propoxy}-phenol Step A. tert-Butyl 4-{2-[2-chloro-4-(3-methyl-1H-pyrazol-1-yl)-phenyl]-3H-imidazo[4,5-b]pyridin-3-yl}phenethylcarbamate tert-Butyl 4-[(3-amino-2-pyridinyl)amino]phenethylcarbamate (0.847 g, 2.58 mmol) was dissolved in anhydrous pyridine and 2-chloro-4-(3-methyl-1H-pyrazol-1-yl)benzoyl chloride (patent WO 9906409) added. The reaction was heated at 100° C. for 18 hours. The solvent was removed and the residue partitioned between water and chloroform. The organic phase was washed with water and brine, dried over anhydrous magnesium sulfate and filtered. The solution was taken to dryness in vacuo and the residue purified by flash chromatography on silica gel Merck-60 (eluant 20:1 chloroform-methanol followed by 1:1 ethyl acetate-hexane) to yield the title compound (0.40 g, 0.756 mmol).

MS ((+)ESI, m/z): 529 [M+H]$^+$

Step B. 2-(4-{2-[2-Chloro-4-(3-methyl-1H-pyrazol-1-yl)phenyl]-3H-imidazo[4,5-b]pyridin-3-yl}phenyl)-1-ethanamine Formate tert-Butyl 4-(2-{2-chloro-4-(3-methyl-1H-pyrazol-1-yl)phenyl]-3H-imidazo[4,5-b]pyridin-3-yl}phenethylcarbamate (0.40 g, 0.756 mmol) was reacted according to Procedure F to provide the title compound (0.212 g, 447 mmol).

Step C. (2S)-1-(4-{[tert-Butyl(diphenyl)silyl]oxy}phenoxy)-3-[(4-{2-[2-chloro-4-(3-methyl-1H-pyrazol-1-yl)phenyl]-3H-imidazo[4,5-b]pyridin-3-yl}phenethyl)amino]-2-propanol 2-(4-{2-[2-Chloro-4-(3-methyl-1 H-pyrazol-1-yl)phenyl]-3H-imidazo[4,5-b]pyridin-3-yl}phenyl)-1-ethanamine formate (0.212 g, 0.447 mmol) was reacted with tert-butyl-(4-oxiranylmethoxy-phenoxy)-diphenyl-silane (0.18 g, 0.44 mmol) according to Procedure G (eluant: 20:1 going to 5:1 chloroform-methanol) to give the title compound (0.18 g, 0.216 mmol).

Step D. 4-{3-[2-(4-{2-[2-Chloro-4-(3-methyl-pyrazol-1-yl)-phenyl]-imidazo[4,5-b]pyridin-3-yl}-phenyl)-ethylamino]-2-hydroxy-propoxy}-phenol (2S)-1-(4-{[tert-Butyl(diphenyl)silyl]oxy}phenoxy)-3-[(4-{2-[2-chloro-4-(3-methyl-1H-pyrazol-1-yl)phenyl]-3H-imidazo[4,5-b]pyridin-3-yl}phenethyl)amino]-2-propanol (0.18 g, 0.216 mmol) was reacted according to Procedure H (eluant: 10:1 going to 5:1 chloroform-methanol containing 1% ammonium hydroxide) to give the title compound (0.08 g, 0.134 mmol).

Mp: 87–89° C.

MS ((+)ESI, m/z): 595 [M+H]$^+$

Anal. Calcd. For $C_{33}H_{31}ClN_6O_3+1.0$ HCl+0.2 $C_2H_6O$+ 0.25 $C_4H_{10}O+1.0 H_2O$: C:61 H:5.61 N:12.41 Found: C:61.41 H:5.32 N: 11.58

EXAMPLE 15

Step A. N-(4-Cyanophenyl)-N'-hexylurea

4-Aminobenzonitrile (11.00 g, 93.1 mmol) was dissolved in anhydrous tetrahydrofuran and hexyl isocyanate (12.43 g, 97.75 mmol) added. The reaction was stirred at reflux for 16 hours. The solvent was removed and the residue partitioned between chloroform and 1N hydrochloric acid. The organic phase was washed with brine, dried over anhydrous magnesium sulfate filtered and the solvent removed in vacuo. The solvent was removed in vacuo and the residue crystallized from diethyl ether to give the title compound (5.2 g, 21.19 mmol).

MS (EI, m/z): 245 [M]+

Step B. Methyl 4-{[(hexylamino)carbonyl]amino}benzenecarboximidoate

Hydrogen chloride gas was bubbled through a methanol solution of N-(4-cyanophenyl)-N'-hexylurea (1.208 g, 4.92 mmol) at 0° C. for 30 minutes. The reaction was sealed and stood at ambient temperature overnight. The solvent was removed in vacuo and the oily residue triturated with diethyl ether. The resulting solid was removed to yield the title compound which was stored in a dry atmosphere.

MS ((−)ESI, m/z): 263 [M−H]−

Step C. tert-Butyl 4-[2-(4-{[(hexylamino)carbonyl]amino}phenyl)-3H-imidazo[4,5-b]pyridin-3-yl]phenethylcarbamate To a solution of anhydrous triethylamine (0.197 mL, 1.46 mmol) and methyl 4-{[(hexylamino)carbonyl]amino}benzenecarboximidoate (0.385 g, 1.18 mmol) in ethanol (30 mL) was added tert-butyl 4-[(3-amino-2-pyridinyl)amino]phenethylcarbamate (0.333 g, 1.01 mmol). The reaction was heated at 90° C. for 36 hours. The solvent was removed in vacuo and the residue combined with a similar residue obtained in an analogous repeat reaction and purified together by flash chromatography on silica gel Merck-60 (eluant 20:1 chloroform-methanol) to yield the title compound (0.35 g, 0.646 mmol).

MS ((+)ESI, m/z): 557 [M+H]+

Step D. N-(4-{3-[4-(2-Aminoethyl)phenyl]-3H-imidazo[4,5-b]pyridin-2-yl}phenyl)-N'-hexylurea Formate tert-Butyl 4-[2-(4-{[(hexylamino)carbonyl]amino}phenyl)-3H-imidazo[4,5-b]pyridin-3-yl]phenethylcarbamate (0.30 g, 0.539 mmol) was reacted according to Procedure F to provide the title compound (0.27 g, 0.539 mmol).

Step E. N-(4-{3-[4-(2-{[(2S)-3-(4-{[tert-butyl(diphenyl)silyl]oxy}phenoxy)-2-hydroxypropyl]amino}ethyl)phenyl]-3H-imidazo[4,5-b]pyridin-2-yl}phenyl)-N'-hexylurea N-(4-{3-[4-(2-aminoethyl)phenyl]-3H-imidazo[4,5-b]pyridin-2-yl}phenyl)-N'-hexylurea formate (0.141 g, 0.280 mmol) was reacted with tert-butyl-(4-oxiranylmethoxyphenoxy)-diphenyl-silane (0.071 g, 0.280 mmol) according to Procedure G (eluant: 20:1 chloroform-methanol) to give the title compound (0.086 g, 0.1 mmol).

Step F. N-hexyl-N'-(4-{3-[4-(2-{[(2S)-2-hydroxy-3-(4-hydroxyphenoxy)propyl]amino}ethyl)phenyl]-3H-imidazo[4,5-b]pyridin-2-yl}phenyl)urea N-(4-{3-[4-(2-{[(2S)-3-(4-{[tert-butyl(diphenyl)silyl]oxy}phenoxy)-2-hydroxypropyl]amino}ethyl)phenyl]-3H-imidazo[4,5-b]pyridin-2-yl}phenyl)-N'-hexylurea (0.086 g, 0.1 mmol) was reacted according to Procedure H (eluant: 10:1 going to 5:1 chloroform-methanol containing 1% ammonium hydroxide) to give the title compound (0.025 g, 0.04 mmol).

MS ((+)ESI, m/z): 623 [M+H]+

Anal. Calcd. For $C_{36}H_{42}N_6O_4$+1.00 HCl+0.50 $H_2O$+0.33 $C_4H_{10}O$: C:64.71 H:6.88 N:12.13

Found: C:64.61 H:6.68 N:11.83

Mp: 110–116° C.

EXAMPLE 16

1-Hexyl-3-{3-[3-(4-{2-[2-hydroxy-3-(4-hydroxyphenoxy)-propylamino]-ethyl}-phenyl)-3H-imidazo[4,5-b]pyridin-2-yl]-phenyl}-urea Step A. Methyl 4-{[(hexylamino)carbonyl]amino}benzoate Methyl 4-aminobenzoate (10.8 g, 71.44 mmol) was dissolved in anhydrous tetrahydrofuran and hexyl isocyanate (9.07 g, 71.31 mmol) added. The reaction was stirred at ambient temperature for 3 days. The solvent was removed and the residue partitioned between chloroform and 1N hydrochloric acid. The organic phase was washed with brine, dried over anhydrous magnesium sulfate filtered and the solvent removed in vacuo. The solvent was removed and the residue crystallized from ethyl acetate to give the title compound (16.15 g, 58.02 mmol).

MS ((+)ESI, m/z): 279 [M+H]+, 296 [M+NH4]+

Step B. 4-{[(Hexylamino)carbonyl]amino}benzoic Acid

Methyl 4-{[(hexylamino)carbonyl]amino}benzoate (5.5 g, 19.76 mmol) was refluxed in methanol (40 mL) and 2.5 N sodium hydroxide (12 mL) for 3 hours. The reaction was cooled and the solvent partially removed in vacuo, poured into ice/hydrochloric acid and the solid removed and washed with water and hexane. The residue was stirred in hexane and filtered to yield the title compound (5.16 g, 19.52 mmol).

MS ((−)ESI, m/z): 263 [M−H]−

Step C. tert-Butyl 4-[2-(3-{[(hexylamino)carbonyl]amino}phenyl)-3H-imidazo[4,5-b]pyridin-3-yl]phenethylcarbamate tert-Butyl 4-[(3-amino-2-pyridinyl)amino]phenethylcarbamate (1.0 g, 3.04 mmol) was dissolved in anhydrous N,N-dimethylformamide (20 mL), 3-{[(hexylamino)carbonyl]amino}benzoic acid (0.805 g, 3.04 mmol) and benzotriazol-1-yloxy-tris(dimethylamino) phosphonium hexafluorophosphate (1.48 g, 3.36 mmol) added together with anhydrous triethylamine (0.722 mL). The reaction was stirred at ambient temperature for 30 minutes. A further portion of 3-{[(hexylamino)carbonyl]amino}benzoic acid (0.08 g) was added and stirring continued for 12 hours. The solvent was removed in vacuo. The residue was dissolved in chloroform, washed with water and brine. The organic layer was dried over anhydrous magnesium sulfate, filtered and the solvent removed in vacuo. The residue was dissolved in anhydrous pyridine and heated at 100° C. for 14 hours. The solvent was removed and the residue co-evaporated with toluene to obtain a solid which was dissolved in chloroform, washed with 1N hydrochloric acid, 1N sodium hydroxide and brine, dried over anhydrous magnesium sulfate and filtered. The solution was taken to dryness in vacuo and the residue purified by flash chromatography on silica gel Merck-60 (eluant: 1:1 going to 2:1 ethyl acetate-hexane) to yield the title compound (0.85 g) which was crystallized from acetone (0.45 g, 0.754 mmol).

MS ((+)ESI, m/z): 557 [M+H]+

Step D. N-(3-{3-[4-(2-aminoethyl)phenyl]-3H-imidazo[4,5-b]pyridin-2-yl}phenyl)-N'-hexylurea Formate tert-Butyl 4-[2-(3-{[(hexylamino)carbonyl]amino}phenyl)-3H-imidazo[4,5-b]pyridin-3-yl]phenethylcarbamate (0.30 g, 0.539 mmol) was reacted according to Procedure F to provide the title compound (0.27 g, 0.539 mmol).

Step E. N-(3-{3-[4-(2-{[(2S)-3-(4-{[tert-butyl(diphenyl)silyl]oxy}phenoxy)-2-hydroxypropyl]amino}ethyl)phenyl]-3H-imidazo[4,5-b]pyridin-2-yl}phenyl)-N'-hexylurea N-(3-{3-[4-(2-aminoethyl)phenyl]-3H-imidazo[4,5-b]pyridin-2-yl}phenyl)-N'-hexylurea formate (0.27 g, 0.539 mmol) was reacted with tert-butyl-(4-oxiranylmethoxyphenoxy)-diphenyl-silane (0.217 g, 0.54 mmol) according to Procedure G (eluant: 20:1 chloroform-methanol) to give the title compound (0.19 g, 0.22 mmol).

Step F. 1-Hexyl-3-{3-[3-(4-{2-[2-hydroxy-3-(4-hydroxy-phenoxy)-propylamino]-ethyl}-phenyl)-3H-imidazo[4,5-b]pyridin-2-yl]-phenyl}-urea N-(3-{3-[4-(2-{[(2S)-3-(4-{[tert-butyl(diphenyl)silyl]oxy}phenoxy)-2-hydroxypropyl]amino}ethyl)phenyl]-3H-imidazo[4,5-b]pyridin-2-yl}phenyl)-N'-hexylurea (0.19 g, 0.22 mmol) was reacted according to Procedure H (eluant: 10:1 going to 5:1 chloroform-methanol containing 1% ammonium hydroxide) to give the title compound (0.067 g, 0.108 mmol).

MS ((−)ESI, m/z): 621 [M−H]⁻

Anal. Calcd. For $C_{36}H_{42}N_6O_4+1.50\,H_2O$: C:66.54 H:6.98 N:12.93 Found: C:66.41 H:6.69 N: 12.52

Mp: 93–95° C.

EXAMPLE 17

1-Hexyl-3-(4-{2-[3-(4-{2-[(2S)-2-hydroxy-3-(4-hydroxy-phenoxy)-propylamino]-ethyl}-phenyl)-3H-imidazo[4,5-b]pyridin-2-yl]-ethyl}-phenyl)-urea Step A. tert-Butyl 4-[2-(4-{[(hexylamino)carbonyl]amino}phenethyl)-3H-imidazo[4,5-b]pyridin-3-yl]phenethylcarbamate tert-Butyl 4-[(3-amino-2-pyridinyl)amino]phenethylcarbamate (1.0 g, 3.04 mmol) was dissolved in anhydrous dichloromethane (25 mL), 3-(4-{[(hexylamino)carbonyl]amino}phenyl)propanoic acid (0.805 g, 3.04 mmol) and benzotriazol-1-yloxy-tris(dimethylamino) phosphonium hexafluorophophate (1.48 g, 3.36 mmol) added together with anhydrous N,N-diisopropylethylamine (0.921 mL). The reaction was stirred at ambient temperature for 30 minutes. A further portion of 3-{[(hexylamino)carbonyl]amino}benzoic acid (0.08 g) was added and stirring continued for 12 hours. The solvent was removed in vacuo. The residue was dissolved in chloroform, washed with water and brine. The organic layer was dried over anhydrous magnesium sulfate, filtered and the solvent removed in vacuo. The residue was dissolved in anhydrous pyridine and heated at 100° C. for 14 hours. The solvent was removed and the residue co-evaporated with toluene to obtain a solid which was dissolved in chloroform, washed with 1N hydrochloric acid, 1N sodium hydroxide and brine, dried over anhydrous magnesium sulfate and filtered. The solution was taken to dryness in vacuo and the residue purified by flash chromatography on silica gel Merck-60 (eluant: 2:1 ethyl acetate-hexane) to yield the title compound (0.6 g, 1.03 mmol).

MS ((+)ESI, m/z): 585 [M+H]⁺

Step B. N-[4-(2-{3-[4-(2-Aminoethyl)phenyl]-3H-imidazo[4,5-b]pyridin-2-yl}ethyl)phenyl]-N'-hexylurea Formate tert-Butyl 4-[2-(4-{[(hexylamino)carbonyl]amino}phenethyl)-3H-imidazo[4,5-b]pyridin-3-yl]phenethylcarbamate (0.60 g, 1.03 mmol) was reacted according to Procedure F to provide the title compound (0.541 g, 1.03 mmol).

Step C. N-[4-(2-{3-[4-(2-{[(2S)-3-(4-{[tert-Butyl(diphenyl)silyl]oxy}phenoxy)-2-hydroxypropyl]amino}ethyl)phenyl]-3H-imidazo[4,5-b]pyridin-2-yl}ethyl)phenyl]-N'-hexylurea N-[4-(2-{3-[4-(2-Aminoethyl)phenyl]-3H-imidazo[4,5-b]pyridin-2-yl}ethyl)phenyl]-N'-hexylurea formate (0.541 g, 1.03 mmol) was reacted with tert-butyl-(4-oxiranylmethoxy-phenoxy)-diphenyl-silane (0.250 g, 0.619 mmol) according to Procedure G (eluant: 20:1 chloroform-methanol) to give the title compound (0.195 g, 0.220 mmol).

Step D. 1-Hexyl-3-(4-{2-[3-(4-{2-[(2S)-2-hydroxy-3-(4-hydroxy-phenoxy)-propylamino]-ethyl}-phenyl)-3H-imidazo[4,5-b]pyridin-2-yl]-ethyl}-phenyl)-urea N-[4-(2-{3-[4-(2-{[(2S)-3-(4-{[tert-Butyl(diphenyl)silyl]oxy}phenoxy)-2-hydroxypropyl]amino}ethyl)phenyl]-3H-imidazo[4,5-b]pyridin-2-yl}ethyl)phenyl]-N'-hexylurea (0.195 g, 0.220 mmol) was reacted according to Procedure H (eluant: 10:1 going to 5:1 chloroform-methanol containing 1% ammonium hydroxide) to give the title compound (0.128 g, 0.197 mmol).

MS ((+)APCI, m/z): 651 [M+H]⁺

Anal. Calcd. For $C_{38}H_{46}N_6O_4+1.00\,H_2O$: C:68.24 H:7.23 N:12.57 Found: C:68.33 H:7.11 N:12.34

Mp: 90–92° C.

What is claimed is:

1. A compound of formula I having the structure

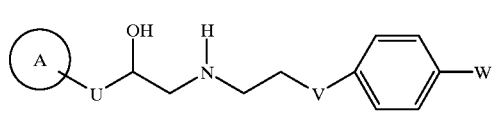

wherein,

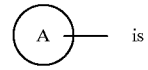 is (a) a phenyl ring substituted with $(R^1)_m$;
(b) a naphthyl ring substituted with $(R^1)_m$; or
(c) a phenyl fused heterocycle selected from the group consisting of

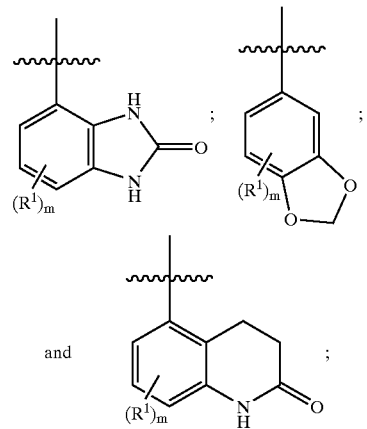

U is —OCH₂— or a bond;
V is O or a bond;
W is

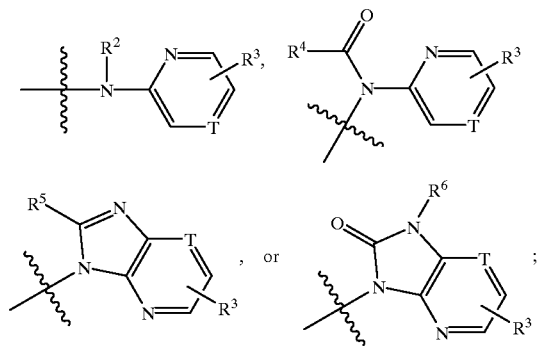

T is CH or N;

R$^1$ is alkyl of 1–8 carbon atoms, aryl of 6–10 carbon atoms, —OR$^7$, cycloalkyl of 3–8 carbon atoms, halogen, cyano, trifluoromethyl, CO$_2$R$^7$, NHCOR$^7$, NHSO$_2$R$^7$, —NR$^7$CONR$^8$R$^9$, —NR$^7$R$^8$, alkenyl of 2–7 carbon atoms, S(O)$_v$R$^7$, NO$_2$, —O(CH$_2$)$_u$CO$_2$R$^7$, —OCONR$^7$R$^8$, —O(CH$_2$)$_s$OR$^7$, or a 5–6 membered heterocyclic ring containing 1 to 4 heteroatoms selected from O, S, and N;

R$^2$, R$^4$, R$^7$, R$^8$, and R$^9$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;

R$^3$ is hydrogen, nitro, halogen, or —NR$^{10}$R$^{11}$;

R$^5$ is hydrogen; alkyl of 1–8 carbon atoms; alkenyl of 2–7 carbon atoms; arylalkyl having 1–8 carbon atoms in the alkyl moiety; alkyl of 1–8 carbon atoms, substituted with 1–4 substituents selected from —OR$^7$ and halogen; —(CH$_2$)$_q$CR$^{12}$R$^{13}$(CH$_2$)$_r$R$^7$; aryl of 6–10 carbon atoms, optionally mono-, di-, or tri-substituted with a substituent selected from the group consisting of halogen, cyano, nitro, trifluoromethyl, alkyl of 1–8 carbons optionally substituted with 1–4 substituents selected from OR$^7$ or halogen, cycloalkyl of 3–8 carbon atoms, aryl of 6–10 carbon atoms, —NHCONR$^7$R$^8$, and —CO$_2$R$^7$; or a 5–6 membered heterocyclic ring containing 1 to 4 heteroatoms selected from O, S, and N, which is optionally mono- or di-substituted with halogen, alkyl of 1–8 carbon atoms, or arylalkyl having 1–8 carbon atoms in the alkyl moiety;

R$^6$ is hydrogen, alkyl of 1–8 carbon atoms, alkenyl of 2–7 carbon atoms, or arylalkyl having 1–8 carbon atoms in the alkyl moiety;

R$^{10}$ and R$^{11}$ are each, independently, hydrogen, alkyl of 1–8 carbon atoms, arylalkyl having 1–8 carbon atoms in the alkyl moiety, —COR$^7$, or —CONR$^7$R$^8$;

R$^{12}$ and R$^{13}$ are each, independently, hydrogen, alkyl of 1–8 carbon atoms, or aryl of 6–10 carbon atoms which is optionally substituted with alkyl of 1–8 carbon atoms or halogen; or R$^{12}$ and R$^{13}$ are taken together to form a spiro fused cycloalkyl ring of 3–8 carbon atoms;

m=0–2;
q=0–5;
r=0–5;
s=1–4;
u=1–4;
v=0–2;

or a pharmaceutically acceptable salt thereof.

2. The compound according to claim 1, wherein

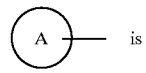

(a) a phenyl ring substituted with (R$^1$)$_m$; or
(b) a phenyl fused heterocycle selected from the group consisting of

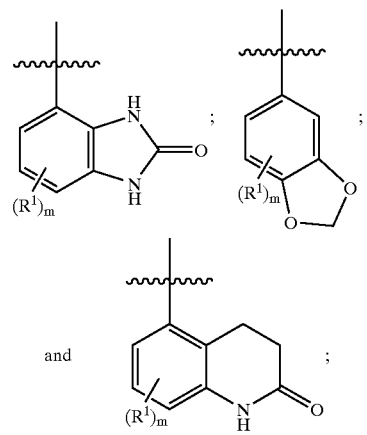

U is —OCH$_2$—;
V is O;
T is CH;
R$^1$ is —OR$^7$;
R$^2$, R$^4$, R$^7$, R$^8$, and R$^9$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;
R$^3$ is hydrogen, nitro, or —NR$^{10}$R$^{11}$;
R$^5$ is hydrogen; alkyl of 1–8 carbon atoms; —(CH$_2$)$_q$CR$^{12}$R$^{13}$(CH$_2$)$_r$R$^7$; aryl of 6–10 carbon atoms, optionally mono-, substituted with a substituent selected from the group consisting of halogen, alkyl of 1–8 carbons optionally substituted with 1–4 substituents selected from OR$^7$ or halogen, cycloalkyl of 3–8 carbon atoms, and —NHCONR$^7$R$^8$; or a 5–6 membered heterocyclic ring containing 1 to 4 heteroatoms selected from O, S, and N, which is optionally mono- or di-substituted with halogen, alkyl of 1–8 carbon atoms, or arylalkyl having 1–8 carbon atoms in the alkyl moiety;
R$^6$ is hydrogen, alkyl of 1–8 carbon atoms, or alkenyl of 2–7 carbon atoms;
R$^{10}$ and R$^{11}$ are each, independently, hydrogen, alkyl of 1–8 carbon atoms, —COR$^7$, or —CONR$^7$R$^8$;
R$^{12}$ and R$^{13}$ are hydrogen;
m=0–1;
q=0–5;
r=0–5;
or a pharmaceutically acceptable salt thereof.

3. The compound of claim 1, which is
a) 4-((2S)-2-Hydroxy-3-{2-[4-(3-nitro-pyridin-2-ylamino)-phenyl]ethylamino}-propoxy)-phenol;
b) 4-((2R)-3-{2-[4-(3-Amino-pyridin-2-ylamino)-phenyl]-ethylamino}-2-hydroxy-propoxy)-phenol;
c) 4-{(2S)-2-Hydroxy-3-[2-(4-imidazo[4,5-b]pyridin-3-yl-phenyl)ethylamino]-propoxy}-phenol;
d) 1-Hexyl-3-[2-(4-{2-[(2S)-2-hydroxy-3-(4-hydroxy-phenoxy)-propylamino]ethyl}-phenylamino)-pyridin-3-yl]-urea;
e) 1-Hexyl-3-{4-[3-(4-{2-[(2S)-2-hydroxy-3-(4-hydroxy-phenoxy)propylamino]-ethyl}-phenyl)-3H-imidazo[4,5-b]pyridin-2-yl]-phenyl}-urea;
f) 4-[(2S)-3-(2-{4-[2-(4-Ethyl-phenyl)-imidazo[4,5-b]pyridin-3-yl]phenyl}-ethylamino)-2-hydroxy-propoxy]-phenol;
g) 4-((2S)-3-{2-[4-(3-Amino-pyridin-2-yloxy)-phenyl]-ethylamino}-2-hydroxy-propoxy)-phenol;

h) N-[2-(4-{2-[(2S)-2-Hydroxy-3-(4-hydroxy-phenoxy)-propylamino]-ethyl}phenylamino)-pyridin-3-yl]-benzamide;

i) 4-((2S)-2-Hydroxy-3-{2-[4-(2-pentyl-imidazo[4,5-b]pyridin-3-yl)phenyl]-ethylamino}-propoxy)-phenol;

j) 3-(4-{2-[(2S)-2-Hydroxy-3-(4-hydroxy-phenoxy)-propylamino]-ethyl}phenyl)-1-isopropenyl-1,3-dihydro-imidazo[4,5-b]pyridin-2-one;

k) 4-[(2S)-3-(2-{4-[2-(4-Cyclohexyl-phenyl)-imidazo[4,5-b]pyridin-3-yl]phenyl}-ethylamino)-2-hydroxy-propoxy]-phenol;

l) 4-((2S)-2-Hydroxy-3-{2-[4-(2-pentyl-imidazo[4,5-b]pyridin-3-yl)phenyl]-ethylamino}-propoxy)-1,3-dihydro-benzoimidazol-2-one;

m) 4-[(2S)-3-(2-{4-[2-(2-Cyclopentyl-ethyl)-imidazo[4,5-b]pyridin-3-yl]phenyl}-ethylamino)-2-hydroxy-propoxy]-phenol;

n) 4-{3-[(2S)-2-(4-{2-[2-Chloro-4-(3-methyl-pyrazol-1-yl)-phenyl]-imidazo[4,5-b]pyridin-3-yl}-phenyl)-ethylamino]-2-hydroxy-propoxy}-phenol;

o) 1-Hexyl-3-{3-[3-(4-{2-(2S)- [2-hydroxy-3-(4-hydroxy-phenoxy)-propylamino]ethyl}-phenyl)-3H-imidazo[4,5-b]pyridin-2-yl]-phenyl} urea;

p) 1-Hexyl-3-(4-{2-[3-(4-{2-[(2S)-2-hydroxy-3-(4-hydroxy-phenoxy)propylamino]-ethyl}-phenyl)-3H-imidazo[4,5-b]pyridin-2-yl]-ethyl}phenyl) urea; or q) 4-[3-(2-{4-[2-(2S)-(2-Cyclopentyl-ethyl)-imidazo[4,5-b]pyridin-3-yl]phenyl}-ethylamino)-2-hydroxy-propoxy]-1,3-dihydro-benzoimidazol-2-one;

or a pharmaceutically acceptable salt thereof.

4. A method of treating metabolic disorders mediated by insulin resistance or hyperglycemia in a mammal in need thereof which comprises providing to said mammal, an effective amount of a compound of formula I having the structure

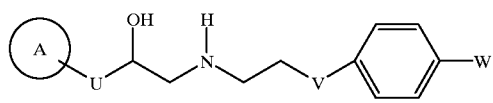

wherein,

 is (a) a phenyl ring substituted with $(R^1)_m$;
(b) a naphthyl ring substituted with $(R^1)_m$; or
(c) a phenyl fused heterocycle selected from the group consisting of

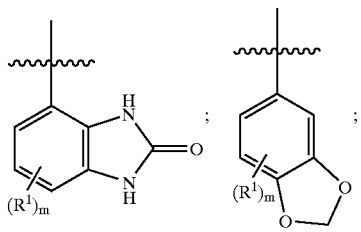

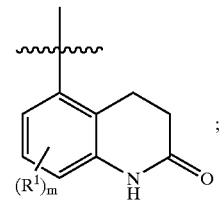

U is —OCH$_2$— or a bond;
V is O or a bond;
W is

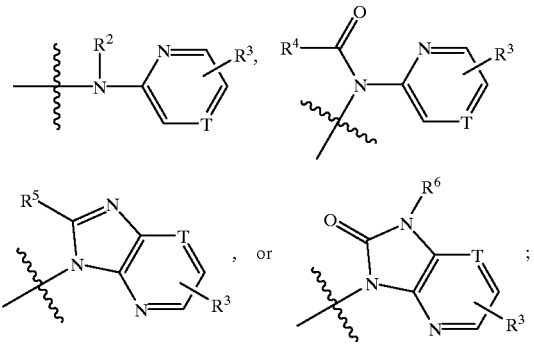

T is CH or N;
$R^1$ is alkyl of 1–8 carbon atoms, aryl of 6–10 carbon atoms, —OR$^7$, cycloalkyl of 3–8 carbon atoms, halogen, cyano, trifluoromethyl, CO$_2$R$^7$, NHCOR$^7$, NHSO$_2$R$^7$, —NR$^7$CONR$^8$R$^9$, —NR$^7$R$^8$, alkenyl of 2–7 carbon atoms, S(O)$_v$R$^7$, NO$_2$, —O(CH$_2$)$_u$CO$_2$R$^7$, —OCONR$^7$R$^8$, —O(CH$_2$)$_s$OR$^7$, or a 5–6 membered heterocyclic ring containing 1 to 4 heteroatoms selected from O, S, and N;
$R^2$, $R^4$, $R^7$, $R^8$, and $R^9$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;
$R^3$ is hydrogen, nitro, halogen, or —NR$^{10}$R$^{11}$;
$R^5$ is hydrogen; alkyl of 1–8 carbon atoms; alkenyl of 2–7 carbon atoms; arylalkyl having 1–8 carbon atoms in the alkyl moiety; alkyl of 1–8 carbon atoms, substituted with 1–4 substituents selected from —OR$^7$ and halogen; —(CH$_2$)$_q$CR$^{12}$R$^{13}$(CH$_2$)$_r$R$^7$; aryl of 6–10 carbon atoms, optionally mono-, di-, or tri-substituted with a substituent selected from the group consisting of halogen, cyano, nitro, trifluoromethyl, alkyl of 1–8 carbons optionally substituted with 1–4 substituents selected from OR$^7$ or halogen, cycloalkyl of 3–8 carbon atoms, aryl of 6–10 carbon atoms, —NHCONR$^7$R$^8$, and —CO$_2$R$^7$; or a 5–6 membered heterocyclic ring containing 1 to 4 heteroatoms selected from O, S, and N, which is optionally mono- or di-substituted with halogen, alkyl of 1–8 carbon atoms, or arylalkyl having 1–8 carbon atoms in the alkyl moiety;
$R^6$ is hydrogen, alkyl of 1–8 carbon atoms, alkenyl of 2–7 carbon atoms, or arylalkyl having 1–8 carbon atoms in the alkyl moiety;
$R^{10}$ and $R^{11}$ are each, independently, hydrogen, alkyl of 1–8 carbon atoms, arylalkyl having 1–8 carbon atoms in the alkyl moiety, —COR$^7$, or —CONR$^7$R$^8$;
$R^{12}$ and $R^{13}$ are each, independently, hydrogen, alkyl of 1–8 carbon atoms, or aryl of 6–10 carbon atoms which is optionally substituted with alkyl of 1–8 carbon atoms or halogen;

or $R^{12}$ and $R^{13}$ are taken together to form a spiro fused cycloalkyl ring of 3–8 carbon atoms;

m=0–2;
q=0–5;
r=0–5;
s=1–4;
u=1–4;
v=0–2;

or a pharmaceutically acceptable salt thereof.

5. A method of treating or inhibiting type II diabetes in a mammal in need thereof which comprises providing to said mammal, an effective amount of a compound of Formula I having the structure

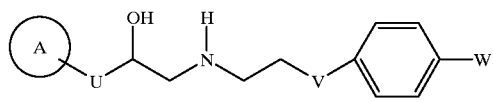

wherein,

 is (a) a phenyl ring substituted with $(R^1)_m$;
(b) a naphthyl ring substituted with $(R^1)_m$; or
(c) a phenyl fused heterocycle selected from the group consisting of

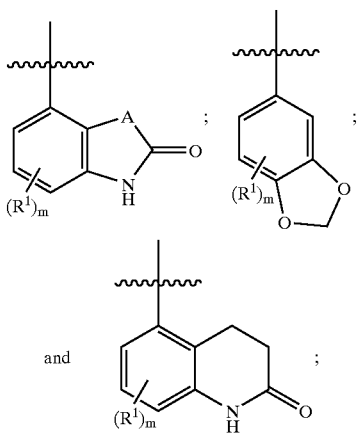

U is —OCH$_2$— or a bond;
V is O or a bond;
W is

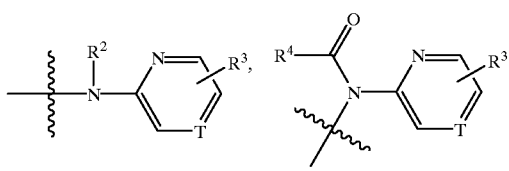

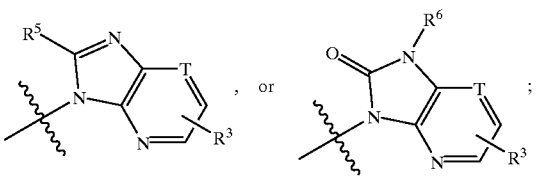

T is CH or N;
$R^1$ is alkyl of 1–8 carbon atoms, aryl of 6–10 carbon atoms, —OR$^7$, cycloalkyl of 3–8 carbon atoms, halogen, cyano, trifluoromethyl, CO$_2$R$^7$, NHCOR$^7$, NHSO$_2$R$^7$, —NR$^7$CONR$^8$R$^9$, —NR$^7$R$^8$, alkenyl of 2–7 carbon atoms, S(O)$_v$R$^7$, NO$_2$, —O(CH$_2$)$_u$CO$_2$R$^7$, —OCONR$^7$R$^8$, —O(CH$_2$)$_s$OR$^7$, or a 5–6 membered heterocyclic ring containing 1 to 4 heteroatoms selected from O, S, and N;
$R^2$, $R^4$, $R^7$, $R^8$, and $R^9$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;
$R^3$ is hydrogen, nitro, halogen, or —NR$^{10}$R$^{11}$;
$R^5$ is hydrogen; alkyl of 1–8 carbon atoms; alkenyl of 2–7 carbon atoms; arylalkyl having 1–8 carbon atoms in the alkyl moiety; alkyl of 1–8 carbon atoms, substituted with 1–4 substituents selected from —OR$^7$ and halogen; —(CH$_2$)$_q$CR$^{12}$R$^{13}$(CH$_2$)$_r$R$^7$; aryl of 6–10 carbon atoms, optionally mono-, di-, or tri-substituted with a substituent selected from the group consisting of halogen, cyano, nitro, trifluoromethyl, alkyl of 1–8 carbons optionally substituted with 1–4 substituents selected from OR$^7$ or halogen, cycloalkyl of 3–8 carbon atoms, aryl of 6–10 carbon atoms, —NHCONR$^7$R$^8$, and —CO$_2$R$^7$; or a 5–6 membered heterocyclic ring containing 1 to 4 heteroatoms selected from O, S, and N, which is optionally mono- or di-substituted with halogen, alkyl of 1–8 carbon atoms, or arylalkyl having 1–8 carbon atoms in the alkyl moiety;
$R^6$ is hydrogen, alkyl of 1–8 carbon atoms, alkenyl of 2–7 carbon atoms, or arylalkyl having 1–8 carbon atoms in the alkyl moiety;
$R^{10}$ and $R^{11}$ are each, independently, hydrogen, alkyl of 1–8 carbon atoms, arylalkyl having 1–8 carbon atoms in the alkyl moiety, —COR$^7$, or —CONR$^7$R$^8$;
$R^{12}$ and $R^{13}$ are each, independently, hydrogen, alkyl of 1–8 carbon atoms, or aryl of 6–10 carbon atoms which is optionally substituted with alkyl of 1–8 carbon atoms or halogen;

or $R^{12}$ and $R^{13}$ are taken together to form a spiro fused cycloalkyl ring of 3–8 carbon atoms;

m=0–2;
q=0–5;
r=0–5;
s=1–4;
u=1–4;
v=0–2;

or a pharmaceutically acceptable salt thereof.

6. A method of modulating glucose levels in a mammal in need thereof which comprises providing to said mammal, an effective amount of a compound of formula I having the structure

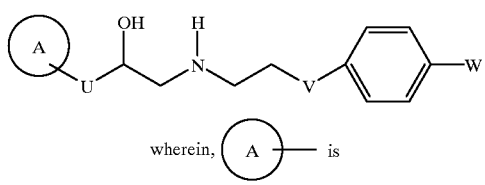

wherein, (A)— is (a) a phenyl ring substituted with $(R^1)_m$;
(b) a naphthyl ring substituted with $(R^1)_m$; or
(c) a phenyl fused heterocycle selected from the group consisting of

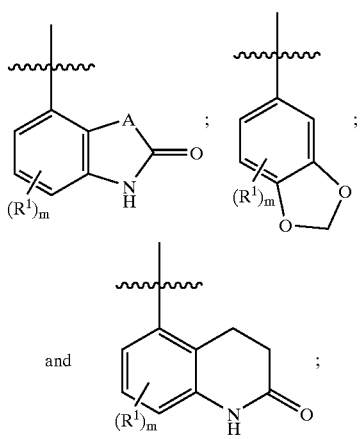

and

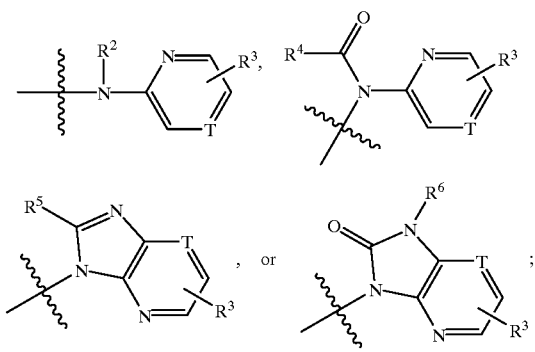

U is —OCH$_2$— or a bond;
V is O or a bond;
W is

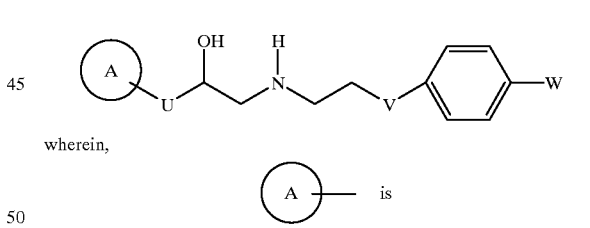

T is CH or N;
$R^1$ is alkyl of 1–8 carbon atoms, aryl of 6–10 carbon atoms, —OR$^7$, cycloalkyl of 3–8 carbon atoms, halogen, cyano, trifluoromethyl, CO$_2$R$^7$, NHCOR$^7$, NHSO$_2$R$^7$, —NR$^7$CONR$^8$R$^9$, —NR$^7$R$^8$, alkenyl of 2–7 carbon atoms, S(O)$_v$R$^7$, NO$_2$, —O(CH$_2$)$_u$CO$_2$R$^7$, —OCONR$^7$R$^8$, —O(CH$_2$)$_s$OR$^7$, or a 5–6 membered heterocyclic ring containing 1 to 4 heteroatoms selected from O, S, and N;
$R^2$, $R^4$, $R^7$, $R^8$, and $R^9$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;
$R^3$ is hydrogen, nitro, halogen, or —NR$^{10}$R$^{11}$;

$R^5$ is hydrogen; alkyl of 1–8 carbon atoms; alkenyl of 2–7 carbon atoms; arylalkyl having 1–8 carbon atoms in the alkyl moiety; alkyl of 1–8 carbon atoms, substituted with 1–4 substituents selected from —OR$^7$ and halogen; —(CH$_2$)$_q$CR$^{12}$R$^{13}$(CH$_2$)$_r$R$^7$; aryl of 6–10 carbon atoms, optionally mono-, di-, or tri-substituted with a substituent selected from the group consisting of halogen, cyano, nitro, trifluoromethyl, alkyl of 1–8 carbons optionally substituted with 1–4 substituents selected from OR$^7$ or halogen, cycloalkyl of 3–8 carbon atoms, aryl of 6–10 carbon atoms, —NHCONR$^7$R$^8$, and —CO$_2$R$^7$; or a 5–6 membered heterocyclic ring containing 1 to 4 heteroatoms selected from O, S, and N, which is optionally mono- or di-substituted with halogen, alkyl of 1–8 carbon atoms, or arylalkyl having 1–8 carbon atoms in the alkyl moiety;
$R^6$ is hydrogen, alkyl of 1–8 carbon atoms, alkenyl of 2–7 carbon atoms, or arylalkyl having 1–8 carbon atoms in the alkyl moiety;
$R^{10}$ and $R^{11}$ are each, independently, hydrogen, alkyl of 1–8 carbon atoms, arylalkyl having 1–8 carbon atoms in the alkyl moiety, —COR$^7$, or —CONR$^7$R$^8$;
$R^{12}$ and $R^{13}$ are each, independently, hydrogen, alkyl of 1–8 carbon atoms, or aryl of 6–10 carbon atoms which is optionally substituted with alkyl of 1–8 carbon atoms or halogen;
or $R^{12}$ and $R^{13}$ are taken together to form a spiro fused cycloalkyl ring of 3–8 carbon atoms;
m=0–2;
q=0–5;
r=0–5;
s=1–4;
u=1–4;
v=0–2;
or a pharmaceutically acceptable salt thereof.

7. A method of treating or inhibiting urinary incontinence in a mammal in need thereof which comprises providing to said mammal an effective amount of a compound of formula I having the structure

I

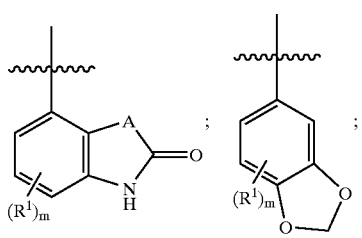

wherein, (A)— is (a) a phenyl ring substituted with $(R^1)_m$;
(b) a naphthyl ring substituted with $(R^1)_m$; or
(c) a phenyl fused heterocycle selected from the group consisting of -continued

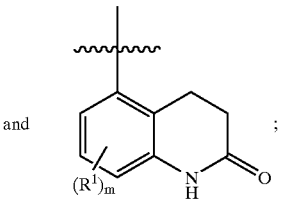
and

U is —OCH$_2$— or a bond;
V is O or a bond;
W is

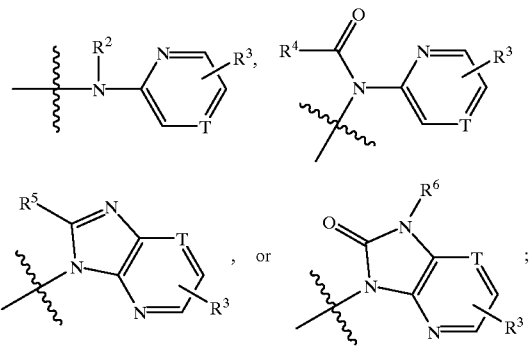

T is CH or N;
R$^1$ is alkyl of 1–8 carbon atoms, aryl of 6–10 carbon atoms, —OR$^7$, cycloalkyl of 3–8 carbon atoms, halogen, cyano, trifluoromethyl, CO$_2$R$^7$, NHCOR$^7$, NHSO$_2$R$^7$, —NR$^7$CONR$^8$R$^9$, —NR$^7$R$^8$, alkenyl of 2–7 carbon atoms, S(O)$_v$R$^7$, NO$_2$, —O(CH$_2$)$_u$CO$_2$R$^7$, —OCONR$^7$R$^8$, —O(CH$_2$)$_s$OR$^7$, or a 5–6 membered heterocyclic ring containing 1 to 4 heteroatoms selected from O, S, and N;
R$^2$, R$^4$, R$^7$, R$^8$, and R$^9$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;
R$^3$ is hydrogen, nitro, halogen, or —NR$^{10}$R$^{11}$;
R$^5$ is hydrogen; alkyl of 1–8 carbon atoms; alkenyl of 2–7 carbon atoms; arylalkyl having 1–8 carbon atoms in the alkyl moiety; alkyl of 1–8 carbon atoms, substituted with 1–4 substituents selected from —OR$^7$ and halogen; —(CH$_2$)$_q$CR$^{12}$R$^{13}$(CH$_2$)$_r$R$^7$; aryl of 6–10 carbon atoms, optionally mono-, di-, or tri-substituted with a substituent selected from the group consisting of halogen, cyano, nitro, trifluoromethyl, alkyl of 1–8 carbons optionally substituted with 1–4 substituents selected from OR$^7$ or halogen, cycloalkyl of 3–8 carbon atoms, aryl of 6–10 carbon atoms, —NHCONR$^7$R$^8$, and —CO$_2$R$^7$; or a 5–6 membered heterocyclic ring containing 1 to 4 heteroatoms selected from O, S, and N, which is optionally mono- or di-substituted with halogen, alkyl of 1–8 carbon atoms, or arylalkyl having 1–8 carbon atoms in the alkyl moiety;
R$^6$ is hydrogen, alkyl of 1–8 carbon atoms, alkenyl of 2–7 carbon atoms, or arylalkyl having 1–8 carbon atoms in the alkyl moiety;
R$^{10}$ and R$^{11}$ are each, independently, hydrogen, alkyl of 1–8 carbon atoms, arylalkyl having 1–8 carbon atoms in the alkyl moiety, —COR$^7$, or —CONR$^7$R$^8$;
R$^{12}$ and R$^{13}$ are each, independently, hydrogen, alkyl of 1–8 carbon atoms, or aryl of 6–10 carbon atoms which is optionally substituted with alkyl of 1–8 carbon atoms or halogen;
or R$^{12}$ and R$^{13}$ are taken together to form a spiro fused cycloalkyl ring of 3–8 carbon atoms;
m=0–2;
q=0–5;
r=0–5;
s=1–4;
u=1–4;
v=0–2;

or a pharmaceutically acceptable salt thereof.

8. A method of treating or inhibiting atherosclerosis, gastrointestinal disorders, neurogenetic inflammation, glaucoma, or ocular hypertension in a mammal in need thereof which comprises providing to said mammal an effective amount of a compound of formula I having the structure

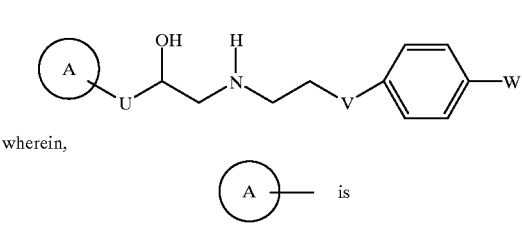

wherein, (A)— is (a) a phenyl ring substituted with (R$^1$)$_m$;
(b) a naphthyl ring substituted with (R$^1$)$_m$; or
(c) a phenyl fused heterocycle selected from the group consisting of

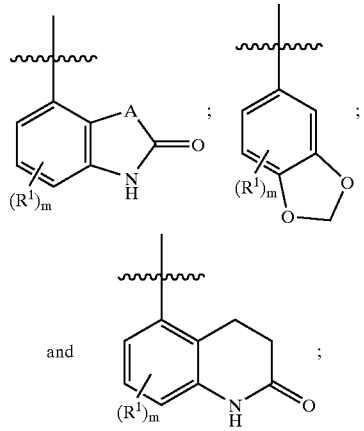

and

U is —OCH$_2$— or a bond;
V is O or a bond;
W is

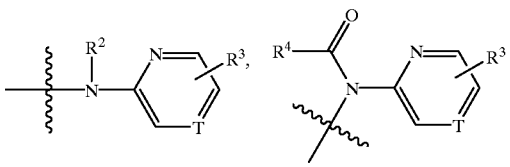

T is CH or N;

R$^1$ is alkyl of 1–8 carbon atoms, aryl of 6–10 carbon atoms, —OR$^7$, cycloalkyl of 3–8 carbon atoms, halogen, cyano, trifluoromethyl, CO$_2$R$^7$, NHCOR$^7$, NHSO$_2$R$^7$, —NR$^7$CONR$^8$R$^9$, —NR$^7$R$^8$, alkenyl of 2–7 carbon atoms, S(O)$_v$R$^7$, NO$_2$, —O(CH$_2$)$_u$CO$_2$R$^7$, —OCONR$^7$R$^8$, —O(CH$_2$)SOR$^7$, or a 5–6 membered heterocyclic ring containing 1 to 4 heteroatoms selected from O, S, and N;

R$^2$, R$^4$, R$^7$, R$^8$, and R$^9$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;

R$^3$ is hydrogen, nitro, halogen, or —NR$^{10}$R$^{11}$;

R$^5$ is hydrogen; alkyl of 1–8 carbon atoms; alkenyl of 2–7 carbon atoms; arylalkyl having 1–8 carbon atoms in the alkyl moiety; alkyl of 1–8 carbon atoms, substituted with 1–4 substituents selected from —OR$^7$ and halogen; —(CH$_2$)$_q$CR$^{12}$R$^{13}$(CH$_2$)$_r$R$^7$; aryl of 6–10 carbon atoms, optionally mono-, di-, or tri-substituted with a substituent selected from the group consisting of halogen, cyano, nitro, trifluoromethyl, alkyl of 1–8 carbons optionally substituted with 1–4 substituents selected from OR$^7$ or halogen, cycloalkyl of 3–8 carbon atoms, aryl of 6–10 carbon atoms, —NHCONR$^7$R$^8$, and —CO$_2$R$^7$; or a 5–6 membered heterocyclic ring containing 1 to 4 heteroatoms selected from O, S, and N, which is optionally mono- or di-substituted with halogen, alkyl of 1–8 carbon atoms, or arylalkyl having 1–8 carbon atoms in the alkyl moiety;

R$^6$ is hydrogen, alkyl of 1–8 carbon atoms, alkenyl of 2–7 carbon atoms, or arylalkyl having 1–8 carbon atoms in the alkyl moiety;

R$^{10}$ and R$^{11}$ are each, independently, hydrogen, alkyl of 1–8 carbon atoms, arylalkyl having 1–8 carbon atoms in the alkyl moiety, —COR$^7$, or —CONR$^7$R$^8$;

R$^{12}$ and R$^{13}$ are each, independently, hydrogen, alkyl of 1–8 carbon atoms, or aryl of 6–10 carbon atoms which is optionally substituted with alkyl of 1–8 carbon atoms or halogen;

or R$^{12}$ and R$^{13}$ are taken together to form a spiro fused cycloalkyl ring of 3–8 carbon atoms;

m=0–2;
q=0–5;
r=0–5;
s=1–4;
u=1–4;
v=0–2;

or a pharmaceutically acceptable salt thereof.

9. A method of increasing the lean meat to fat ratio in a mammal in need thereof, which comprises providing to said mammal an effective amount of a compound of formula I having the structure wherein, Ⓐ— is (a) a phenyl ring substituted with (R$^1$)$_m$;
(b) a naphthyl ring substituted with (R$^1$)$_m$; or
(c) a phenyl fused heterocycle selected from the group consisting of and U is —OCH$_2$— or a bond;
V is O or a bond;
W is T is CH or N;

R$^1$ is alkyl of 1–8 carbon atoms, aryl of 6–10 carbon atoms, —OR$^7$, cycloalkyl of 3–8 carbon atoms, halogen, cyano, trifluoromethyl, CO$_2$R$^7$, NHCOR$^7$, NHSO$_2$R$^7$, —NR$^7$CONR$^8$R$^9$, —NR$^7$R$^8$, alkenyl of 2–7 carbon atoms, S(O)$_v$R$^7$, NO$_2$, —O(CH$_2$)$_u$CO$_2$R$^7$, —OCONR$^7$R$^8$, —O(CH$_2$)$_s$OR$^7$, or a 5–6 membered heterocyclic ring containing 1 to 4 heteroatoms selected from O, S, and N;

R$^2$, R$^4$, R$^7$, R$^8$, and R$^9$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;

R$^3$ is hydrogen, nitro, halogen, or —NR$^{10}$R$^{11}$;

R$^5$ is hydrogen; alkyl of 1–8 carbon atoms; alkenyl of 2–7 carbon atoms; arylalkyl having 1–8 carbon atoms in the alkyl moiety; alkyl of 1–8 carbon atoms, substituted with 1–4 substituents selected from —OR$^7$ and halogen; —(CH$_2$)$_q$CR$^{12}$R$^{13}$(CH$_2$)$_r$R$^7$; aryl of 6–10 carbon atoms, optionally mono-, di-, or tri-substituted with a substituent selected from the group consisting of halogen, cyano, nitro, trifluoromethyl, alkyl of 1–8 carbons optionally substituted with 1–4 substituents selected from OR$^7$ or halogen, cycloalkyl of 3–8 carbon atoms, aryl of 6–10 carbon atoms, —NHCONR$^7$R$^8$, and —CO$_2$R$^7$; or a 5–6 membered heterocyclic ring containing 1 to 4 heteroatoms selected from O, S, and N, which is optionally mono- or di-substituted with halogen, alkyl of 1–8 carbon atoms, or arylalkyl having 1–8 carbon atoms in the alkyl moiety;

R$^6$ is hydrogen, alkyl of 1–8 carbon atoms, alkenyl of 2–7 carbon atoms, or arylalkyl having 1–8 carbon atoms in the alkyl moiety;

R$^{10}$ and R$^{11}$ are each, independently, hydrogen, alkyl of 1–8 carbon atoms, arylalkyl having 1–8 carbon atoms in the alkyl moiety, —COR$^7$, or —CONR$^7$R$^8$;

R$^{12}$ and R$^{13}$ are each, independently, hydrogen, alkyl of 1–8 carbon atoms, or aryl of 6–10 carbon atoms which is optionally substituted with alkyl of 1–8 carbon atoms or halogen;

or R$^{12}$ and R$^{13}$ are taken together to form a spiro fused cycloalkyl ring of 3–8 carbon atoms;

m=0–2;
q=0–5;
r=0–5;
s=1–4;
u=1–4;
v=0–2;

or a pharmaceutically acceptable salt thereof.

10. A pharmaceutical composition which comprises a compound of formula I having the structure

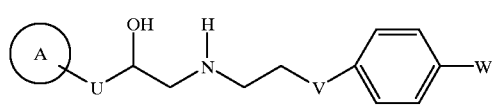

I wherein,

 is (a) a phenyl ring substituted with (R$^1$)$_m$;
(b) a naphthyl ring substituted with (R$^1$)$_m$; or
(c) a phenyl fused heterocycle selected from the group consisting of

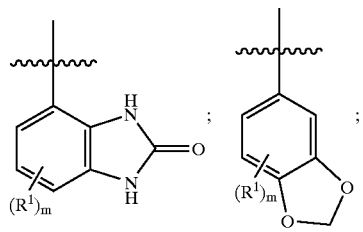

-continued

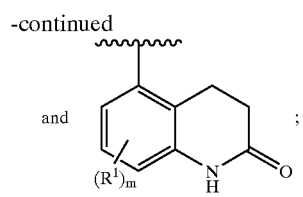

and

U is —OCH$_2$— or a bond;
V is O or a bond;
W is

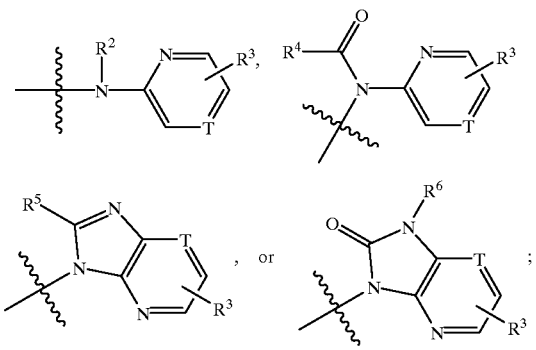

T is CH or N;

R$^1$ is alkyl of 1–8 carbon atoms, aryl of 6–10 carbon atoms, —OR$^7$, cycloalkyl of 3–8 carbon atoms, halogen, cyano, trifluoromethyl, CO$_2$R$^7$, NHCOR$^7$, NHSO$_2$R$^7$, —NR$^7$CONR$^8$R$^9$, —NR$^7$R$^8$, alkenyl of 2–7 carbon atoms, S(O)$_v$R$^7$, NO$_2$, —O(CH$_2$)$_u$CO$_2$R$^7$, —OCONR$^7$R$^8$, —O(CH$_2$)$_s$OR$^7$, or a 5–6 membered heterocyclic ring containing 1 to 4 heteroatoms selected from O, S, and N;

R$^2$, R$^4$, R$^7$, R$^8$, and R$^9$ are each, independently, hydrogen, alkyl of 1–8 carbon atoms, aryl of 6–10 carbon atoms, cycloalkyl of 3–8 carbon atoms, or arylalkyl having 1–8 carbon atoms in the alkyl moiety;

R$^3$ is hydrogen, nitro, halogen, or —NR$^{10}$R$^{11}$;

R$^5$ is hydrogen; alkyl of 1–8 carbon atoms; alkenyl of 2–7 carbon atoms; arylalkyl having 1–8 carbon atoms in the alkyl moiety; alkyl of 1–8 carbon atoms, substituted with 1–4 substituents selected from —OR$^7$ and halogen; —(CH$_2$)$_q$CR$^{12}$R$^{13}$(CH$_2$)$_r$R$^7$; aryl of 6–10 carbon atoms, optionally mono-, di-, or tri-substituted with a substituent selected from the group consisting of halogen, cyano, nitro, trifluoromethyl, alkyl of 1–8 carbons optionally substituted with 1–4 substituents selected from OR$^7$ or halogen, cycloalkyl of 3–8 carbon atoms, aryl of 6–10 carbon atoms, —NHCONR$^7$R$^8$, and —CO$_2$R$^7$; or a 5–6 membered heterocyclic ring containing 1 to 4 heteroatoms selected from O, S, and N, which is optionally mono- or di-substituted with halogen, alkyl of 1–8 carbon atoms, or arylalkyl having 1–8 carbon atoms in the alkyl moiety;

R$^6$ is hydrogen, alkyl of 1–8 carbon atoms, alkenyl of 2–7 carbon atoms, or arylalkyl having 1–8 carbon atoms in the alkyl moiety;

$R^{10}$ and $R^{11}$ are each, independently, hydrogen, alkyl of 1–8 carbon atoms, arylalkyl having 1–8 carbon atoms in the alkyl moiety, —$COR^7$, or —$CONR^7R^8$;

$R^{12}$ and $R^{13}$ are each, independently, hydrogen, alkyl of 1–8 carbon atoms, or aryl of 6–10 carbon atoms which is optionally substituted with alkyl of 1–8 carbon atoms or halogen;

or $R^{12}$ and $R^{13}$ are taken together to form a spiro fused cycloalkyl ring of 3–8 carbon atoms;

m=0–2;
q=0–5;
r=0–5;
s=1–4;
u=1–4;
v=0–2;

or a pharmaceutically acceptable salt thereof, and a pharmaceutical carrier.

* * * * *